(12) United States Patent
Akahoshi et al.

(10) Patent No.: US 12,398,190 B2
(45) Date of Patent: Aug. 26, 2025

(54) METHOD OF PRODUCING CAR-T CELLS, NUCLEIC ACID-INTRODUCING CARRIER AND KIT

(71) Applicants: KABUSHIKI KAISHA TOSHIBA, Tokyo (JP); SHINSHU UNIVERSITY, Nagano (JP)

(72) Inventors: Eiichi Akahoshi, Tokyo (JP); Mitsuko Ishihara, Tokyo (JP); Yozo Nakazawa, Matsumoto (JP); Daisuke Morita, Matsumoto (JP)

(73) Assignees: KABUSHIKI KAISHA TOSHIBA, Tokyo (JP); SHINSHU UNIVERSITY, Nagano (JP)

( * ) Notice: Subject to any disclaimer, the term of this patent is extended or adjusted under 35 U.S.C. 154(b) by 772 days.

(21) Appl. No.: 17/195,357

(22) Filed: Mar. 8, 2021

(65) Prior Publication Data
US 2021/0246424 A1 Aug. 12, 2021

Related U.S. Application Data

(63) Continuation of application No. PCT/IB2020/056879, filed on Jul. 22, 2020.

(30) Foreign Application Priority Data

Jul. 23, 2019 (JP) .................................. 2019-135549

(51) Int. Cl.
| | |
|---|---|
| *C07K 14/705* | (2006.01) |
| *A61K 40/11* | (2025.01) |
| *A61K 40/31* | (2025.01) |
| *A61K 40/42* | (2025.01) |
| *C07K 16/28* | (2006.01) |
| *C12N 5/0783* | (2010.01) |
| *C12N 15/113* | (2010.01) |

(52) U.S. Cl.
CPC ............ *C07K 14/705* (2013.01); *A61K 40/11* (2025.01); *A61K 40/31* (2025.01); *A61K 40/4211* (2025.01); *C07K 16/2809* (2013.01); *C07K 16/2818* (2013.01); *C12N 5/0636* (2013.01); *C12N 15/113* (2013.01); *C12N 2501/998* (2013.01); *C12N 2510/00* (2013.01)

(58) Field of Classification Search
CPC ............... C12N 5/0636; C12N 15/113; C12N 2501/998; C12N 2510/00; C12N 15/907; C12N 2310/00; C12N 2800/90; C12N 9/1241; C12N 15/85; C12N 15/88; C07K 14/705; C07K 16/2809; C07K 16/2818; C07K 16/2803; C07K 2317/622; C07K 2319/03; C07K 2319/33; C07K 14/7051; A61K 9/0019; A61K 9/08; A61K 47/18; A61K 48/00; A61K 2039/5156; A61K 9/1272; A61K 39/0011; C12P 21/02
See application file for complete search history.

(56) References Cited

U.S. PATENT DOCUMENTS

| | | | |
|---|---|---|---|
| 11,548,857 B2 * | 1/2023 | Ishihara | C07D 295/13 |
| 2010/0154070 A1 | 6/2010 | Xu et al. | |
| 2015/0110721 A1 | 4/2015 | Conrad et al. | |
| 2016/0145348 A1 | 5/2016 | Stephan | |
| 2018/0016337 A1 | 1/2018 | Chao et al. | |
| 2018/0051265 A1 | 2/2018 | Cooper | |
| 2018/0289742 A1 * | 10/2018 | Nishio | C07K 19/00 |
| 2019/0167812 A1 | 6/2019 | Ishihara | |
| 2019/0202923 A1 | 7/2019 | Nakazawa et al. | |
| 2019/0343880 A1 | 11/2019 | Hosoi et al. | |
| 2019/0374655 A1 | 12/2019 | Kabadi | |
| 2020/0000723 A1 | 1/2020 | Ishihara et al. | |
| 2020/0270217 A1 | 8/2020 | Ishihara et al. | |
| 2022/0047517 A1 * | 2/2022 | Ishihara | A61K 9/5123 |
| 2022/0195401 A1 * | 6/2022 | Akahoshi | C12Y 207/07 |
| 2023/0099139 A1 * | 3/2023 | Ishihara | C07D 295/15 |
| | | | 514/218 |

FOREIGN PATENT DOCUMENTS

| | | |
|---|---|---|
| CN | 109477114 A | 3/2019 |
| JP | 2002-529439 A | 9/2002 |
| JP | 2004-159501 A | 6/2004 |

(Continued)

OTHER PUBLICATIONS

Nakazawa et al. "Optimization of the PiggyBac transposon system for the sustained genetic modification of human T-lymphocytes." Journal of immunotherapy (Hagerstown, Md.: 1997) 32.8 (2009): 826 (Year: 2009).*

Lima et al. "Cationic lipid-DNA complexes in gene delivery: from biophysics to biological applications." Advanced drug delivery reviews 47.2-3 (2001): 277-294 (Year: 2001).*

Daisuke Morita et al., "Enhanced Expression of Anti-CD19 Chimeric Antigen Receptor in piggyBac Transposon-Engineered T Cells", Molecular Therapy: Methods & Clinical Development (vol. 8), Mar. 2018, pp. 131-140, DOI: 10.1016/j.omtm.2017.12.003.

(Continued)

*Primary Examiner* — Maria G Leavitt
*Assistant Examiner* — Alexander W Nicol
(74) *Attorney, Agent, or Firm* — Oblon, McClelland, Maier & Neustadt, L.L.P.

(57) ABSTRACT

According to one embodiment, there is provided a method of producing a gene modification T cell (CAR-T cells) which expresses a chimeric antigen receptor (CAR). This method includes stimulating a cell population containing a T cell with an antibody which activates the T cell, bringing the cell population into contact with a nucleic acid-introducing carrier, wherein the nucleic acid-introducing carrier containing a lipid particle, a first nucleic acid and containing a CAR gene, and a second nucleic acid containing a transposase gene encapsulated in the lipid particle, and culturing the cell population after the contacting.

13 Claims, 11 Drawing Sheets
Specification includes a Sequence Listing.

(56) References Cited

FOREIGN PATENT DOCUMENTS

| | | |
|---|---|---|
| JP | 2008-545375 A | 12/2008 |
| JP | 2015-500835 A | 1/2015 |
| JP | 2016-540534 A | 12/2016 |
| JP | WO2017/061615 A1 | 4/2017 |
| JP | 2018-509151 A | 4/2018 |
| JP | 2018-533573 A | 11/2018 |
| JP | 2019-507579 A | 3/2019 |
| JP | 2019-511566 A | 4/2019 |
| JP | 2021-16370 A | 2/2021 |
| WO | WO 00/27795 A1 | 5/2000 |
| WO | WO 2013/086354 A1 | 6/2013 |
| WO | WO 2014/153114 A1 | 9/2014 |
| WO | WO 2017/061615 A1 | 4/2017 |
| WO | WO 2017/075531 A1 | 5/2017 |
| WO | WO 2018/052142 A1 | 3/2018 |
| WO | WO 2018/073393 A2 | 4/2018 |
| WO | WO 2018/110374 A1 | 6/2018 |
| WO | WO 2021/014224 A1 | 1/2021 |

OTHER PUBLICATIONS

Nakazawa, Y. et al., "WO 2017061615-A/2: Method for Preparing Gene-Modified T Cells Expressing Chimeric Antigen Receptor", GenBank: LX096012.1, Apr. 13, 2017, 2 pages, https://www.mcbi.nlm.nih.gov/nuccore/LX096012.1.

Zimowska, G. J. et al., "Trichoplusia ni transposon piggyBac Tn-pBac3 transposase gene, partial cds", GenBank: DQ236237.1, 2006, 2 pages. https://www.ncbi.nlm.nih.gov/nucleotide/DQ236237.1?report=genbank&log$=nuclalign&blast_rank=12&RID=8CHJ9D8B01N.

Martin A Maier et al., "Biodegradable Lipids Enabling Rapidly Eliminated Lipid Nanoparticles for Systemic Delivery of RNAi Therapeutics", Molecular Therapy (vol. 21, No. 8), Aug. 2013, pp. 1570-1578 DOI: 10.1038/mt.2013.124.

Yi Zhao et al., "Lipid Nanoparticles for Gene Delivery", Advances in Genetics (vol. 88), 2014, pp. 13-36 (pp. 1-21) DOI: 10.1016/B978-0-12-800148-6.00002-X.

Yan Zheng et al., "PiggyBac transposon system with polymeric gene carrier transfected into human T cells", American journal of translational research (vol. 11, No. 11), 2019, pp. 7126-7136, downloaded by the EPO on Sep. 25, 2020 from: https://www.ncbi.nlm.nih.gov/pmc/articles/PMC6895516/pdf.aitr0011-7126.pdf.

International Search Report and Written Opinion issued on Jul. 22, 2020, in PCT/IB2020/056879, filed Oct. 12, 2020.

Khurana, Bharat et al., "Lipoplexes versus nanoparticles: pDNA/siRNA delivery", Drug Delivery (vol. 20, No. 2), 2013, pp. 57-64, DOI: 10.3109/10717544.2012.752419.

Zhou, Kejin et al., "Modular degradable dendrimers enable small RNAs to extend survival in an aggressive liver cancer model", Proceedings of the National Academy of Sciences (vol. 113, No. 3), 2016, pp. 520-525, DOI: 10.1073/pnas.1520756113.

Japanese Office Action issued in Japanese Application No. No. 2023-130389, on Jul. 23, 2024, 3 pages. (with English Machine Translation provided by Global Dossier).

\* cited by examiner

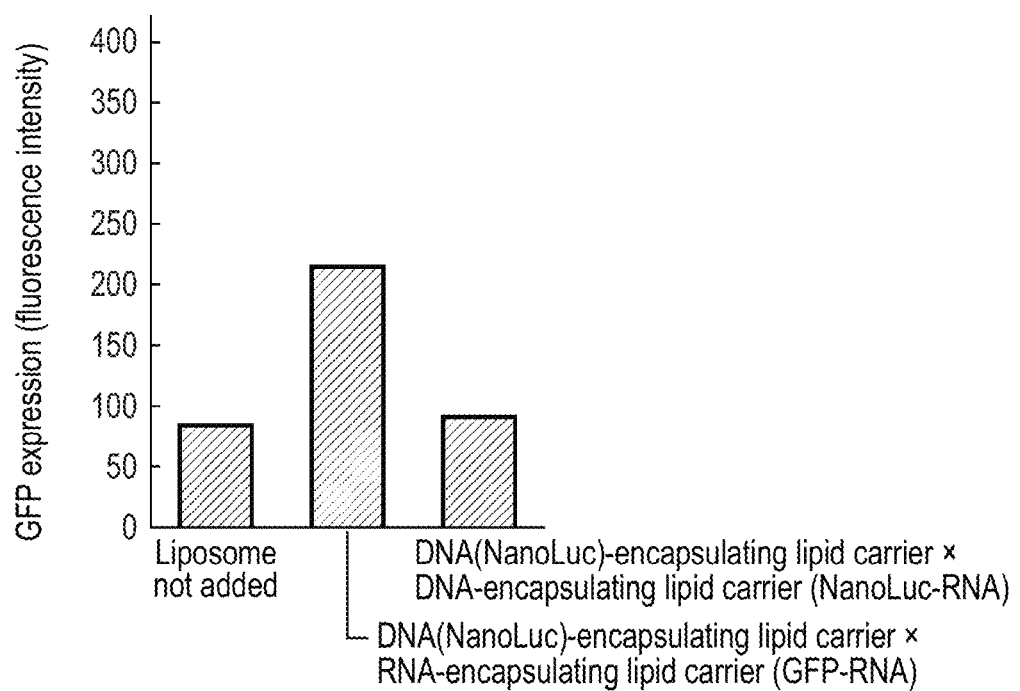
F I G. 13

SEQUENCE LISTING

```
<160> NUMBER OF SEQ ID NOS: 6

<210> SEQ ID NO 1
<211> LENGTH: 4536
<212> TYPE: DNA
<213> ORGANISM: Artificial
<220> FEATURE:
<223> OTHER INFORMATION: 5'IR_CAR gene_3'IR

<400> SEQUENCE: 1
tttaacccta gaaagatagt ctgcgtaaaa ttgacgcatg cattcttgaa atattgctct        60
ctctttctaa atagcgcgaa tccgtcgctg tgcatttagg acatctcagt cgccgcttgg       120
agctcccgtg aggcgtgctt gtcaatgcgg taagtgtcac tgattttgaa ctataacgac       180
cgcgtgagtc aaaatgacgc atgattatct tttacgtgac ttttaagatt taactcatac       240
gataattata ttgttatttc atgttctact tacgtgataa cttattatat atatattttc       300
ttgttataga taagatcttc aatattggcc attagccata ttattcattg gttatatagc       360
ataaatcaat attggctatt ggccattgca tacgttgtat ctatatcata atatgtacat       420
ttatattggc tcatgtccaa tatgaccgcc atgttggcat tgattattga ctagttatta       480
atagtaatca attacggggt cattagttca tagcccatat atggagttcc gcgttacata       540
acttacggta aatggcccgc ctggctgacc gcccaacgac ccccgcccat tgacgtcaat       600
aatgacgtat gttcccatag taacgccaat agggactttc cattgacgtc aatgggtgga       660
gtatttacgg taaactgccc acttggcagt acatcaagtg tatcatatgc caagtccgcc       720
ccctattgac gtcaatgacg gtaaatggcc cgcctggcat tatgcccagt acatgacctt       780
acgggacttt cctacttggc agtacatcta cgtattagtc atcgctatta ccatggtgat       840
gcggttttgg cagtacacca atgggcgtgg atagcggttt gactcacggg gatttccaag       900
tctccacccc attgacgtca atgggagttt gttttggcac caaaatcaac gggactttcc       960
```

```
aaaatgtcgt aacaactgcg atcgcccgcc ccgttgacgc aaatgggcgg taggcgtgta   1020
cggtgggagg tctatataag cagagctcgt ttagtgaacc gtcagatcac tagaagcttt   1080
attgcggtag tttatcacag ttaaattgct aacgcagtca gtgcttctga cacaacagtc   1140
tcgaacttaa gctgcagtga ctctcttaag gtagccttgc agaagttggt cgtgaggcac   1200
tgggcaggta agtatcaagg ttacaagaca ggtttaagga gaccaataga aactgggctt   1260
gtcgagacag agaagactct tgcgtttctg ataggcacct attggtctta ctgacatcca   1320 cttttgccttt ctctccacag gtgtccactc ccagttcaat tacagctctt aaggctagag   1380
tacttaatac gactcactat aggctagcct cgagctcaag cttcgaattc gaatggccat   1440
ggagtttggg ctgagctggc ttttcttgt ggctatttta aaaggtgtcc agtgctctag   1500
agacatccag atgacacaga ctacatcctc cctgtctgcc tctctgggag acagagtcac   1560
catcagttgc agggcaagtc aggacattag taaatattta aattggtatc agcaaaaacc   1620
agatggaact gttaaactcc tgatctacca tacatcaaga ttacactcag gagtcccatc   1680
aaggttcagt ggcagtgggt ctggaacaga ttattctctc accattagca acctggagca   1740
agaagatatt gccacttact tttgccaaca gggtaatacg cttccgtaca cgttcggagg   1800
ggggaccaag ctggagctga aacgtggtgg tggtggttct ggtggtggtg gttctggtaa   1860
gcctatccct aaccctctcc tcggtctcga ttctacgggc ggcggcggct ccggtggtgg   1920
tggatccgag gtgcagctgc agcagtctgg acctggcctg gtggcgccct cacagagcct   1980
gtccgtcaca tgcactgtct caggggtctc attacccgac tatggtgtaa gctggattcg   2040
ccagcctcca cgaaagggtc tggagtggct gggagtaata tgggggtagtg aaaccacata   2100 ctataattca gctctcaaat ccagactgac catcatcaag gacaactcca agagccaagt   2160
tttcttaaaa atgaacagtc tgcaaactga tgacacagcc atttactact gtgccaaaca   2220
ttattactac ggtggtagct atgctatgga ctactgggc caaggacca cggtcaccgt   2280 ctcctcgtac gtcaccgtct cttcacagga tcccgccgag cccaaatctc ctgacaaaac   2340
tcacacatgc ccaccgtgcc cagcacctga actcctgggg ggaccgtcag tcttcctctt   2400
ccccccaaaa cccaaggaca cctcatgat ctccccggacc cctgaggtca catgcgtggt   2460
ggtggacgtg agccacgaag accctgaggt caagttcaac tggtacgtgg acggcgtgga   2520
ggtgcataat gccaagacaa agccgcggga ggagcagtac aacagcacgt accgtgtggt   2580
cagcgtcctc accgtcctgc accaggactg gctgaatggc aaggagtaca agtgcaaggt   2640
ctccaacaaa gccctcccag cccccatcga gaaaaccatc tccaaagcca aagggcagcc   2700
ccgagaacca caggtgtaca ccctgccccc atcccgggat gagctgacca agaaccaggt   2760
cagcctgacc tgcctggtca aaggcttcta tcccagcgac atcgccgtgg agtgggagag   2820
caatgggcaa ccggagaaca actacaagac cacgcctccc gtgctggact ccgacggctc   2880
cttcttcctc tacagcaagc tcaccgtgga caagagcagg tggcagcagg ggaacgtctt   2940
ctcatgctcc gtgatgcatg aggctctgca caaccactac acgcagaaga gcctctccct   3000
gtctccgggt aaaaaagatc ccaaattttg ggtgctggtg gtggttggtg gagtcctggc   3060
ttgctatagc ttgctagtaa cagtggcctt tattattttc tgggtgagga gtaagaggag   3120
caggctcctg cacagtgact acatgaacat gactccccgc cgccccgggc ccacccgcaa   3180
gcattaccag ccctatgccc caccacgcga cttcgcagcc tatcgctcca gagtgaagtt   3240
cagcaggagc gcagacgccc ccgcgtacca gcagggccag aaccagctct ataacgagct   3300
```

| | | | | |
|---|---|---|---|---|
| caatctagga | cgaagagagg | agtacgatgt | tttggacaag | agacgtggcc gggaccctga | 3360 |
| gatgggggga | aagccgagaa | ggaagaaccc | tcaggaaggc | ctgtacaatg aactgcagaa | 3420 |
| agataagatg | gcggaggcct | acagtgagat | tgggatgaaa | ggcgagcgcc ggaggggcaa | 3480 |
| ggggcacgat | ggcctttacc | agggtctcag | tacagccacc | aaggacacct acgacgccct | 3540 |
| tcacatgcag | gccctgcctc | ctcgctaagc | atgctagcta | tagttctaga ggtaccggtt | 3600 |
| gttaacgtta | gccggctacg | tatactccgg | aatattaata | ggcctaggat gcatatggcg | 3660 |
| gccgcttccc | tttagtgagg | gttaatgctt | cgagcagaca | tgataagata cattgatgag | 3720 |
| tttggacaaa | ccacaactag | aatgcagtga | aaaaaatgct | ttatttgtga aatttgtgat | 3780 |
| gctattgctt | tatttgtaac | cattataagc | tgcaataaac | aagttaacaa caacaattgc | 3840 |
| attcatttta | tgtttcaggt | tcaggggag | atgtgggagg | ttttttaaag caagtaaaac | 3900 |
| ctctacaaat | gtggtaaaat | ccgataagga | tcgatccggg | ctggcgtaat agcgaagagg | 3960 |
| cccgcaccga | tcgcccttcc | caacagttgc | gcagcctgaa | tggcgaatgg acgcgcctg | 4020 |
| tagcggcgca | ttaagcgcgg | cgggtgtggt | ggttacgcgc | agcgtgaccg ctacacttgc | 4080 |
| cagcgcccta | gcgcccgctc | ctttcgcttt | cttcccttcc | tttctcgcca cgttcgcccg | 4140 |
| atagcgataa | ggatccgcgt | atggtgcact | ctcagtacaa | tctgctctga tgccgcatag | 4200 |
| ttaagccagc | cccgacaccc | gccaacaccc | gctgacgcgc | cctgacgggc ttgtctgctc | 4260 |
| ccggcatccg | cttacagaca | agctgtgacc | gtctccggga | ttttgttact ttatagaaga | 4320 |
| aattttgagt | ttttgttttt | ttttaataaa | taaatacca | taaataaatt gtttgttgaa | 4380 |
| tttattatta | gtatgtaagt | gtaaatataa | taaaacttaa | tatctattca aattaataaa | 4440 |
| taaacctcga | tatacagacc | gataaaacac | atgcgtcaat | tttacgcatg attatcttta | 4500 |
| acgtacgtca | caatatgatt | atctttctag | ggttaa | | 4536 |

<210> SEQ ID NO 2
<211> LENGTH: 1785
<212> TYPE: DNA
<213> ORGANISM: human

<400> SEQUENCE: 2

| | | | | |
|---|---|---|---|---|
| aatgggtagt | tctttagacg | atgagcatat | cctctctgct | cttctgcaaa gcgatgacga | 60 |
| gcttgttggt | gaggattctg | acagtgaaat | atcagatcac | gtaagtgaag atgacgtcca | 120 |
| gagcgataca | gaagaagcgt | ttatagatga | ggtacatgaa | gtgcagccaa cgtcaagcgg | 180 |
| tagtgaaata | ttagacgaac | aaaatgttat | tgaacaacca | ggttcttcat ggcttctaa | 240 |
| cagaatcttg | accttgccac | agaggactat | tagaggtaag | aataaacatt gttggtcaac | 300 |
| ttcaaagtcc | acgaggcgta | gccgagtctc | tgcactgaac | attgtcagat ctcaaagagg | 360 |
| tccgacgcgt | atgtgccgca | atatatatga | cccactttta | tgcttcaaac tatttttac | 420 |
| tgatgagata | atttcggaaa | ttgtaaaatg | gacaaatgct | gagatatcat tgaaacgtcg | 480 |
| ggaatctatg | acaggtgcta | catttcgtga | cacgaatgaa | gatgaaatct atgctttctt | 540 |
| tggtattctg | gtaatgacag | cagtgagaaa | agataaccac | atgtccacag atgacctctt | 600 |
| tgatcgatct | ttgtcaatgg | tgtacgtctc | tgtaatgagt | cgtgatcgtt ttgattttt | 660 |
| gatacgatgt | cttagaatgg | atgacaaaag | tatacggccc | acacttcgag aaaacgatgt | 720 |
| atttactcct | gttagaaaaa | tatgggatct | ctttatccat | cagtgcatac aaaattacac | 780 |
| tccagggct | catttgacca | tagatgaaca | gttacttggt | tttagaggac ggtgtccgtt | 840 |
| taggatgtat | atcccaaaca | agccaagtaa | gtatggaata | aaaatcctca tgatgtgtga | 900 |

```
cagtggtacg aagtatatga taaatggaat gccttatttg ggaagaggaa cacagaccaa    960
cggagtacca ctcggtgaat actacgtgaa ggagttatca aagcctgtgc acggtagttg   1020
tcgtaatatt acgtgtgaca attggttcac ctcaatccct ttggcaaaaa acttactaca   1080
agaaccgtat aagttaacca ttgtgggaac cgtgcgatca aacaaacgcg agataccgga   1140
agtactgaaa acagtcgct ccaggccagt gggaacatcg atgttttgtt ttgacggacc   1200
ccttactctc gtctcatata aaccgaagcc agctaagatg gtatacttat tatcatcttg   1260
tgatgaggat gcttctatca acgaaagtac cggtaaaccg caaatggtta tgtattataa   1320
tcaaactaaa ggcggagtgg acacgctaga ccaaatgtgt tctgtgatga cctgcagtag   1380
gaagacgaat aggtggccta tggcattatt gtacggaatg ataaacattg cctgcataaa   1440 ttctttatt atatacagcc ataatgtcag tagcaaggga gaaaaggttc aaagtcgcaa   1500
aaaatttatg agaaaccttt acatgagcct gacgtcatcg tttatgcgta agcgtttaga   1560
agctcctact ttgaagagat atttgcgcga taatatctct aatattttgc caaatgaagt   1620
gcctggtaca tcagatgaca gtactgaaga gccagtaatg aaaaaacgta cttactgtac   1680
ttactgcccc tctaaaataa ggcgaaaggc aaatgcatcg tgcaaaaaat gcaaaaaagt   1740
tatttgtcga gagcataata ttgatatgtg ccaaagttgt ttctg                  1785

<210> SEQ ID NO 3
<211> LENGTH: 20
<212> TYPE: PRT
<213> ORGANISM: Artificial Sequence
<220> FEATURE:
<223> OTHER INFORMATION: Nucleic acid condensing peptide

<400> SEQUENCE: 3

Arg Gln Arg Gln Arg Tyr Tyr Arg Gln Arg Gln Arg Gly Gly Arg Arg
1               5                   10                  15

Arg Arg Arg Arg
            20

<210> SEQ ID NO 4
<211> LENGTH: 13
<212> TYPE: PRT
<213> ORGANISM: Artificial Sequence
<220> FEATURE:
<223> OTHER INFORMATION: Nucleic acid condensing peptide

<400> SEQUENCE: 4

Arg Gln Arg Gln Arg Gly Gly Arg Arg Arg Arg Arg Arg
1               5                   10

<210> SEQ ID NO 5
<211> LENGTH: 21
<212> TYPE: PRT
<213> ORGANISM: Artificial Sequence
<220> FEATURE:
<223> OTHER INFORMATION: Nucleic acid condensing peptide

<400> SEQUENCE: 5

Arg Arg Arg Arg Arg Arg Tyr Tyr Arg Gln Arg Gln Arg Gly Gly Arg
1               5                   10                  15

Arg Arg Arg Arg Arg
            20

<210> SEQ ID NO 6
<211> LENGTH: 39
```

```
<212> TYPE: PRT
<213> ORGANISM: human

<400> SEQUENCE: 6

Gly Asn Gln Ser Ser Asn Phe Gly Pro Met Lys Gly Gly Asn Phe Gly
1               5                   10                  15

Gly Arg Ser Ser Gly Pro Tyr Gly Gly Gly Gln Tyr Phe Ala Lys
                20                  25                  30

Pro Arg Asn Gln Gly Gly Tyr
            35
```

METHOD OF PRODUCING CAR-T CELLS, NUCLEIC ACID-INTRODUCING CARRIER AND KIT

CROSS-REFERENCE TO RELATED APPLICATIONS

This application is a Continuation Application of PCT Application No. PCT/IB2020/056879, filed Jul. 22, 2020 and based upon and claiming the benefit of priority from Japanese Patent Application No. 2019-135549, filed Jul. 23, 2019, the entire contents of all of which are incorporated herein by reference.

FIELD

Embodiments described herein relate generally to a method of producing CAR-T cells, a nucleic acid-introducing carrier and a kit.

BACKGROUND

A CAR-T cellular therapy which uses T cells whose gene is modified to produce a chimeric antigen receptor (CAR), that is, CAR-T cells, is currently attracting attention because the curative effect to tumor is very high. In this method, a CAR gene is introduced into a T cell sampled from a patient, to produce a CAR-T cell, which is administered to the patient. The administered CAR-T cell kills tumor cells encountered in the body of the patient.

In the production of CAR-T cells, generally, the virus vector method and electroporation are used for introduction of the CAR gene. However, these methods require a complicated operation especially in the gene introduction and the culturing process, and especially, when using the virus vector, an exclusive cell-culturing facility is required, thus raising an economical problem of very high treatment costs.

Under these circumstances, there is a demand for a method which can easily and efficiently introduce CAR gene into a T cell.

BRIEF DESCRIPTION OF THE DRAWINGS

FIG. 13 is a graph illustrating a test result (GFP fluorescence intensity) in Example 4.

DETAILED DESCRIPTION

In general, according to one embodiment, there is provided a method of producing a gene modification T cell (CAR-T cells) which expresses a chimeric antigen receptor (CAR). The method comprises: stimulating a cell population containing T cells with an antibody which activates T cell; a gene introducing a gene by bringing the cell population into contact with a nucleic acid-introducing carrier after the stimulating, wherein the nucleic acid-introducing carrier contains a lipid particle, a first nucleic acid containing a CAR gene and a second nucleic acid containing a transposase gene encapsulated in the lipid particle; and culturing of culturing the cell population after the introducing the gene.

Nucleic acid-introducing carrier, a production method of CAR-T cells and a kit thereof according to embodiments will be described below with reference to the accompanying drawings. The drawings are schematic diagrams for assist understanding of the embodiments, and shapes, dimensions, ratios and the like thereof are different from actual ones. However, these drawings are appropriately changed in design in consideration of the following description and known techniques.

—Nucleic Acid-Introducing Carrier

Figure 1:
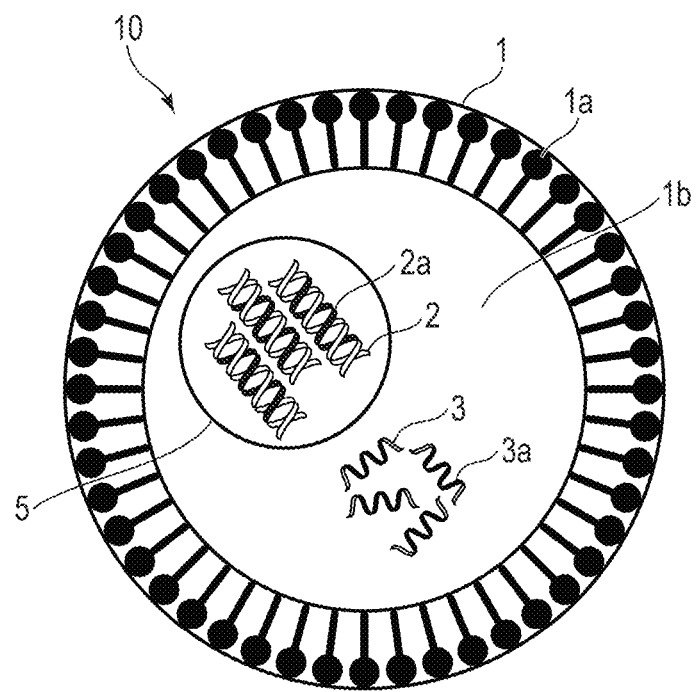
FIG. 1 is a cross section showing an example of a nucleic acid-introducing carrier of an embodiment.

As will be described in detail, the nucleic acid-introducing carrier of the embodiments is used for production of CAR-T cells, and can introduce CAR genes into cells by bringing the nucleic acid-introducing carrier into contact with the cells. An example of the nucleic acid-introducing carrier will be described with reference to FIG. 1.

A nucleic acid-introducing carrier 10 comprises, for example, a lipid particle 1 and a first nucleic acid 2 and a second nucleic acid 3 encapsulated in the lipid particle 1. The first nucleic acid 2 contains a sequence 2a coding for CAR gene (to be referred to as "CAR gene sequence", hereinafter). The second nucleic acid 3 contains a sequence 3a coding for transposase gene (to be referred to as "transposase gene sequence", hereinafter). The first nucleic acid 2 and the second nucleic acid 3 are encapsulated in the lipid particle 1 while being condensed with a nucleic acid condensation peptide 5, for example.

Hereinafter, each structural component will be described in detail.

(Lipid Particle)

The lipid particle 1 of the embodiment is substantially a spherical hollow body made from a lipid membrane in which a plurality of lipid molecules 1a are arranges in sequence by noncovalent bond. In a central lumen 1b thereof, the first nucleic acid 2 and the second nucleic acid 3 are encapsulated. The lipid particle 1 may be a lipid monomolecular membrane or a lipid double membrane.

Further, the lipid particle 1 may be formed from a single membrane or a multilayered membrane.

The material of the lipid particle 1 may be composed from base lipids listed below as examples, but it is preferable to further contain the first lipid compound and/or the second lipid compound, listed below as examples, other than the base lipid.

For example, as the base lipid, lipids which are major ingredients of a biomembrane can be used. The base lipid is phospholipid or sphingolipid, for example, diacyl phosphatidylcholine, diacyl phosphatidyl ethanolamine, ceramide, sphingomyelin, dihydrosphingomyelin, cephalin or cerebroside or any combination thereof and the like.

Preferable usable examples of the base lipid are 1,2-dioleoyl-sn-glycero-3-phosphoethanolamine (DOPE),
1,2-stearoyl-sn-glycero-3-phosphoethanolamine (DSPE),
1,2-dipalmitoyl-sn-glycero-3-phosphatidylcholine (DPPC),
1-palmitoyl-2-oleoyl-sn-glycero-3-phosphatidylcholine (POPC),
1,2-di-O-octadecyl-3-trimethyl ammonium propane (DOTMA),
1,2-dioleoyl-3-dimethyl ammonium propane (DODAP),
1,2-dimyristoyl-3-dimethyl ammonium propane (14:0 DAP)
1,2-dipalmitoyl-3-dimethyl ammonium propane (16:0 DAP),
1,2-distearoyl-3-dimethyl ammonium propane (18:0 DAP),
N-(4-carboxy benzyl)-N,N-dimethyl-2,3-bis (oleoyloxy) propane (DOBAQ),
1,2-dioleoyl-3-trimethyl ammonium propane (DOTAP),
1,2-dioleoyl-sn-glycero-3-phosphochlorin (DOPC),
1,2-dilinoleoyl-sn-glycero-3-phosphocholine (DLPC),
1,2-dioleoyl-sn-glycero-3-phospho-L-serine (DOPS), or
Cholesterol
   or any combination of thereof. In particular, DOTAP is a cationic lipid, and therefore it is preferable because an acid dissociation constant of the lipid particle 1 can be adjusted by its content. The above-listed base lipids are easy to fuse with cell membranes, and therefore when, particularly, diacyl phosphatidylcholine and diacyl phosphatidyl ethanolamine are used, it is preferable because the structure of the lipid particle 1 and the particle diameter are easy controlled and also they are easy to fuse with cell membranes. It is preferable that the length of the hydrocarbon chain of the acyl group included in the lipid be $C_{10}$ to $C_{20}$. The hydrocarbon chain may be a saturated hydrocarbon group or an unsaturated hydrocarbon group.

The base lipid may be contained at nearly 100% to all lipid molecules 1$a$ contained in the lipid particle 1. Or, when the lipid particle 1 contain the first and/or second lipid compounds, it is preferable that the base lipid be contained at approximately 30% to approximately 80% (in molar ratio) to the all lipid molecules 1$a$.

The first lipid compound is, for example, biodegradable. The first lipid compound can be represented by a formula of $$Q\text{-}CHR_2$$

(where
Q represents a nitrogen-containing aliphatic group which contains two or more tertiary nitrogen elements and does not contain oxygen,
R is independently an aliphatic group of $C_{12}$ to $C_{24}$, and at least one R contains, in its main chain or side chain, a linking group LR selected from the group consisting of —C(=O)—O—, —O—C(=O)—, —O—C(=O)—O—, —S—C(=O)—, —C(=O)—S—, —C(=O)—NH—, and —NHC(=O)—).

When the lipid particle 1 contains the first lipid compound, the surface of the lipid particle 1 becomes non-cationic, and therefore difficulties in the cell introduction is reduced, thereby improving the nucleic acid introduction efficiency.

Here, it is preferable to use a lipid, for example, having the structure represented by the formulas provided below as the first lipid compound, because such a lipid exhibits a superior nucleic acid introduction efficiency.

[Chemical Formula 1]

(1-01)

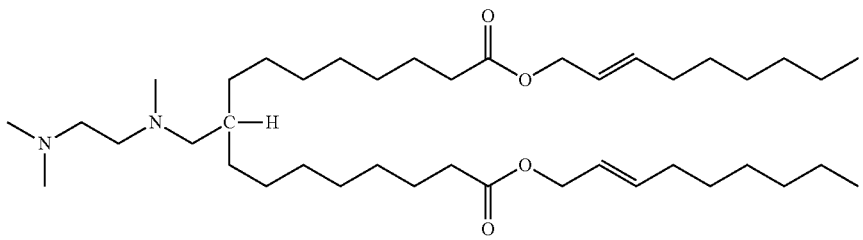

(1-02)

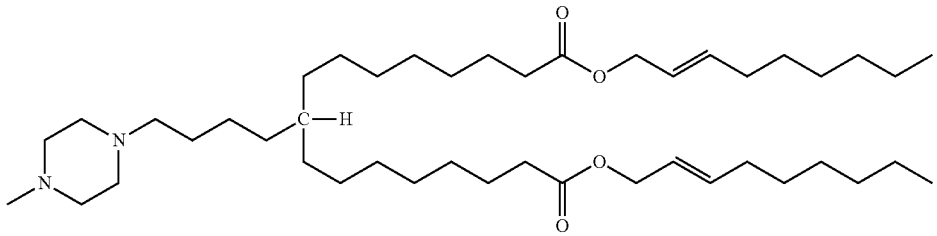

-continued
(1-03)
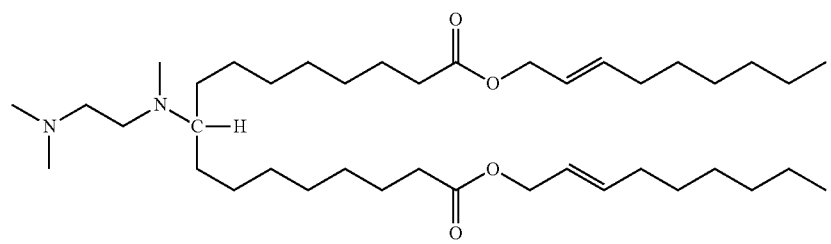
(1-04)
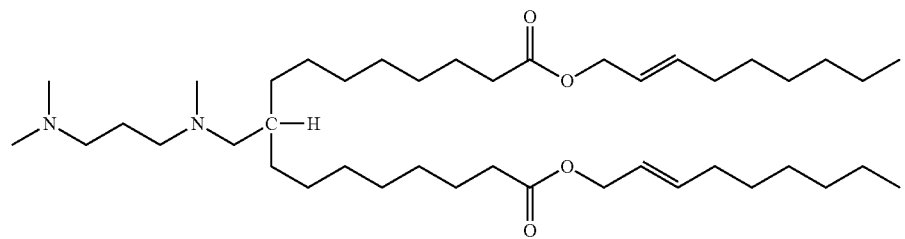
(1-05)
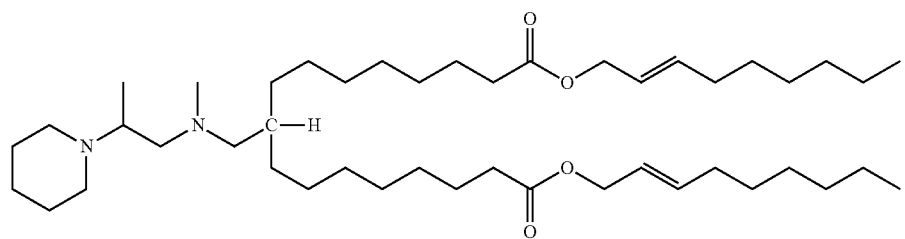
(1-06)
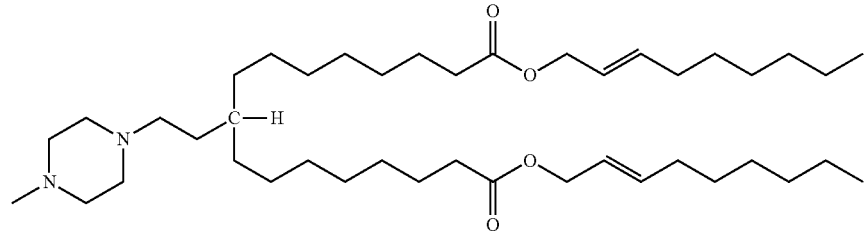
(1-07)
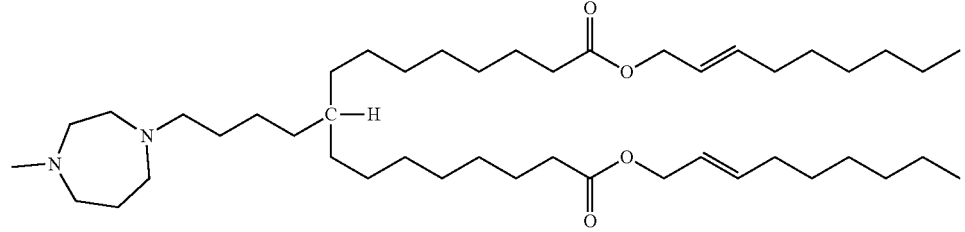
(1-08)
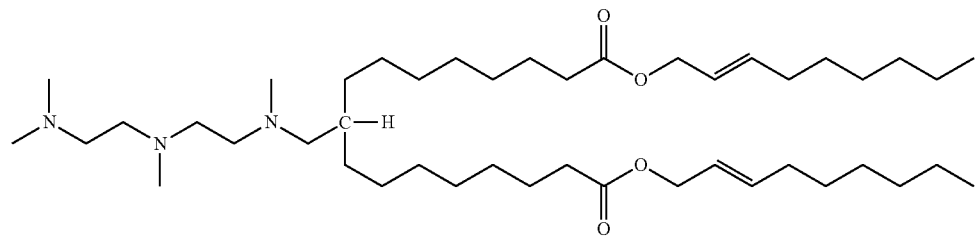

-continued
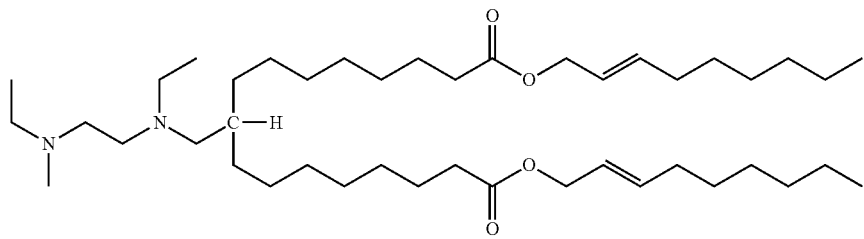
(1-09)
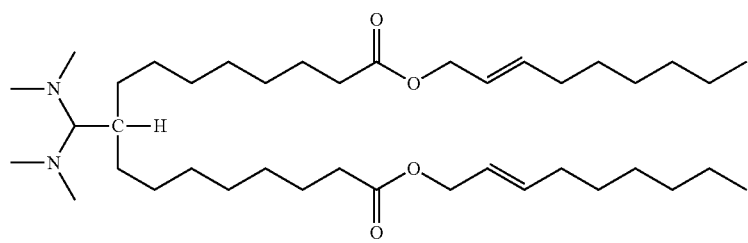
(1-10)
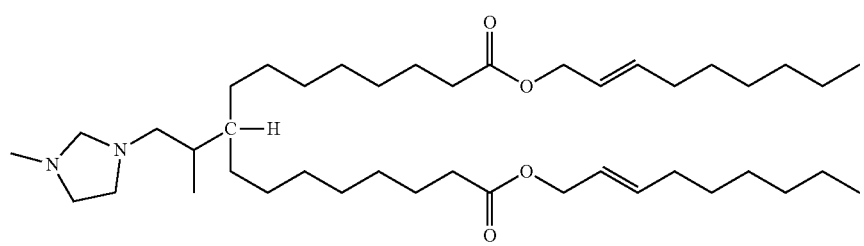
(1-11)
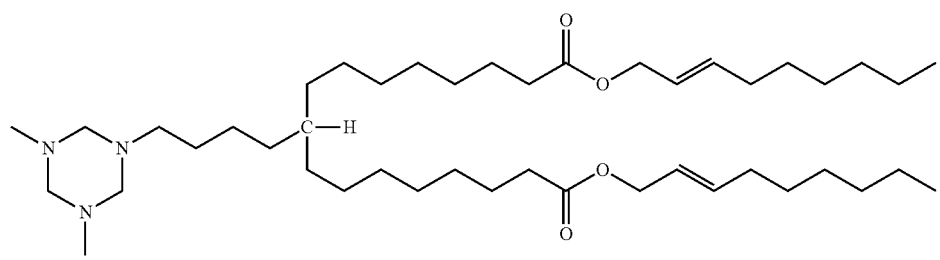
(1-12)
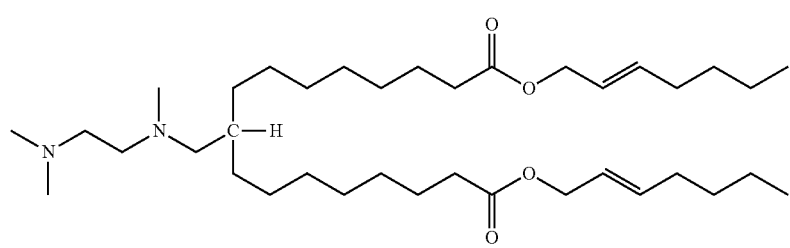
(1-13)
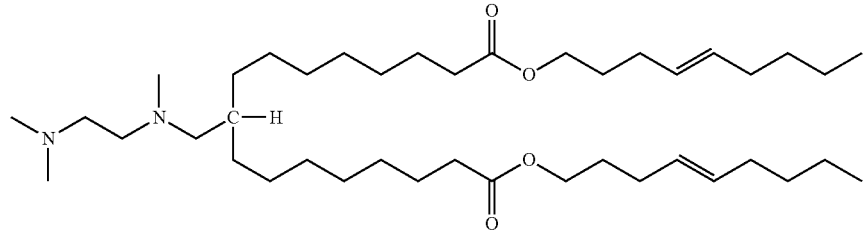
(1-14)

-continued
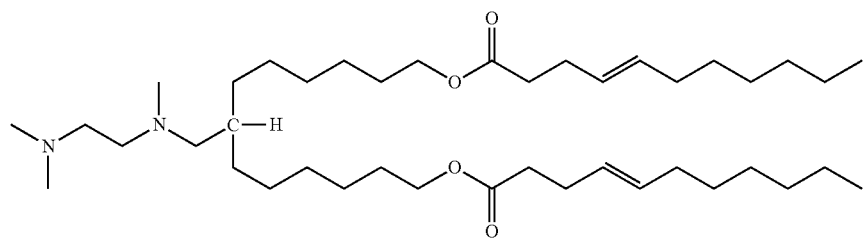
(1-15)
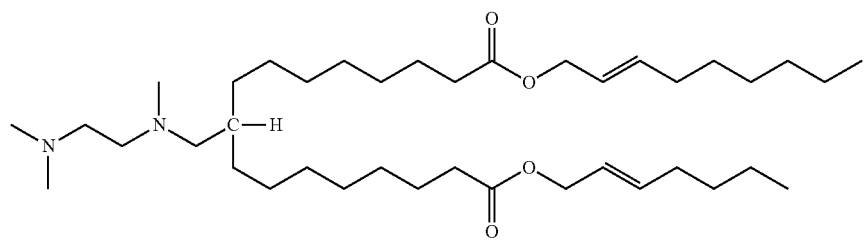
(1-16)
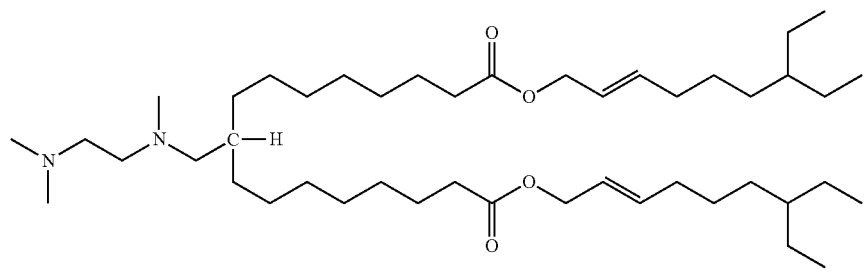
(1-17)
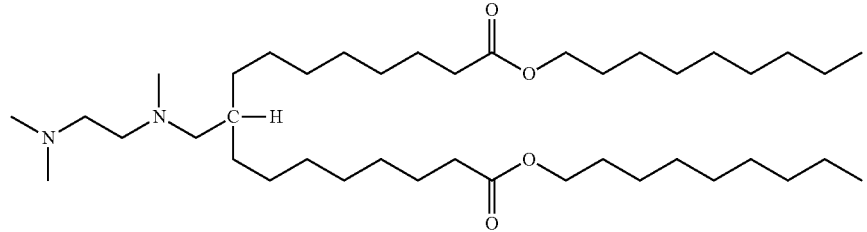
(1-18)
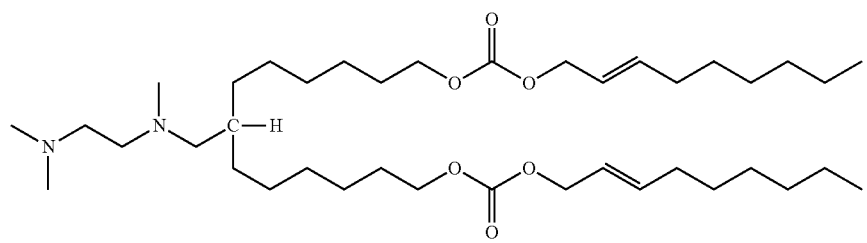
(1-19)
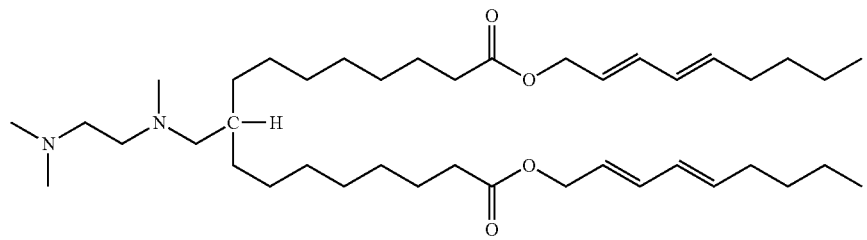
(1-20)

(1-21)

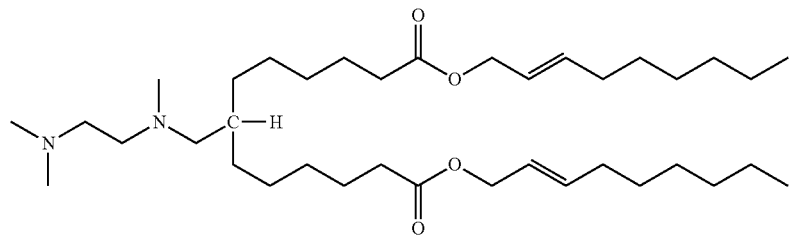

The second lipid compound is, for example, biodegradable. The second lipid compound can be represented by a formula of

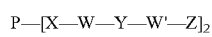

(where,
P represents alkyleneoxy containing one or more ether bonds in its main chain,
X represents a divalent linking group including a tertiary amine structure,
W is independently $C_1$ to $C_6$ alkylene,
Y represents a divalent linking group selected independently from the group consisting a single bond, ether bond, carboxylic ester bond, thiocarboxylic ester bond, thioester bond, amide bond, carbamate bond and bond, respectively,
W' is independently a single bond or $C_1$ to $C_6$ alkylene, and
Z is independently a fat-soluble vitamin residue, sterol residue or $C_{12}$ to $C_{22}$ aliphatic hydrocarbon group).

When the second lipid compound is included, oxygen of the ether bond contained in P forms hydrogen bond with the encapsulated nucleic acid, and therefore the amount of encapsulated nucleic acid increases.

It is preferable to use the second lipid compound, for example, having a structure of the followings because of its higher encapsulated nucleic acid amount.

[Chemical Formula 2]

(2-01)

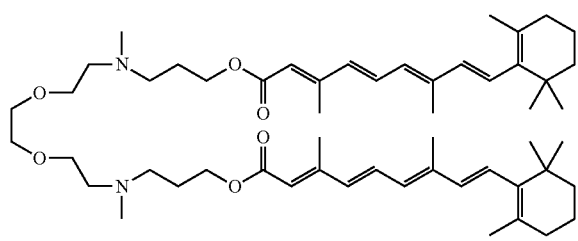

(2-02)

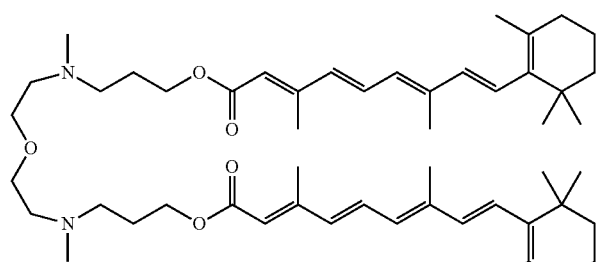

(2-03)

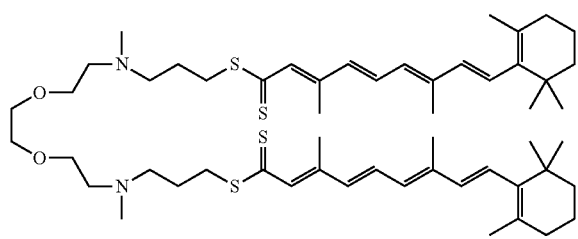

(2-04)

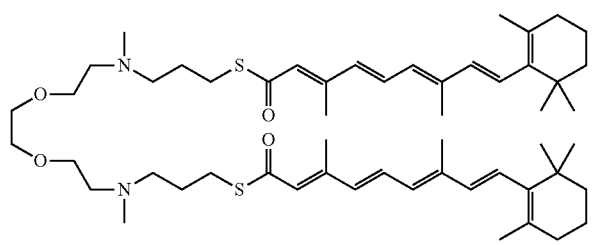

(2-05)

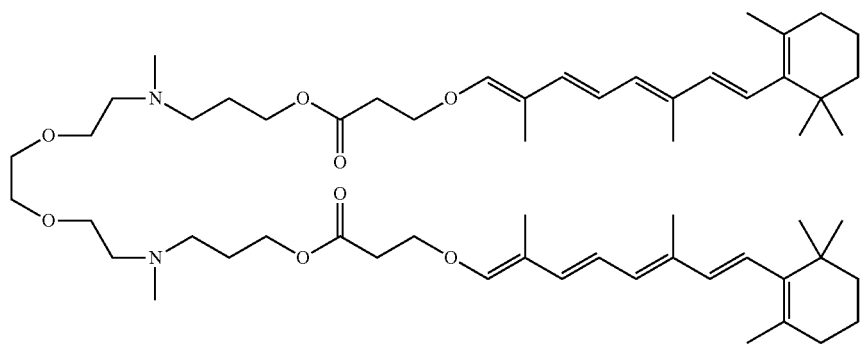

-continued
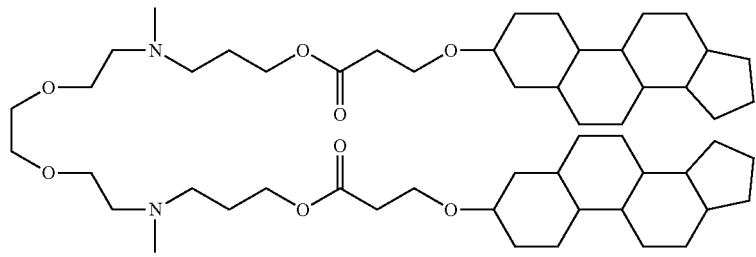
(2-06)
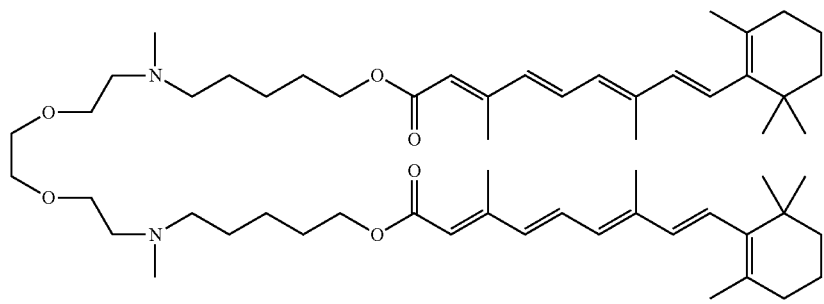
(2-07)
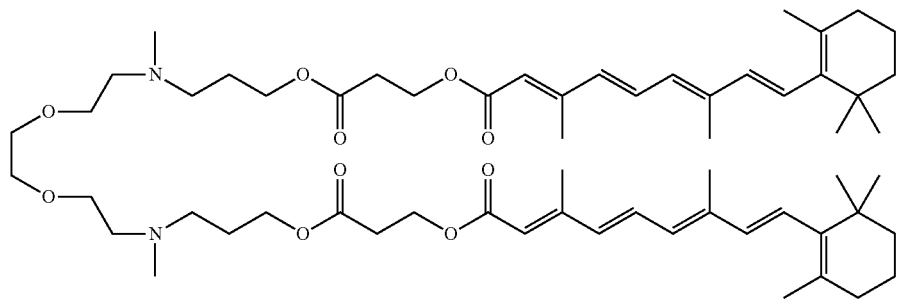
(2-08)
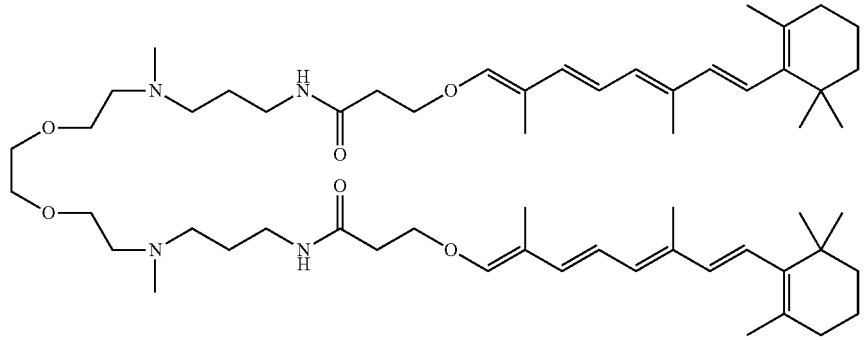
(2-09)
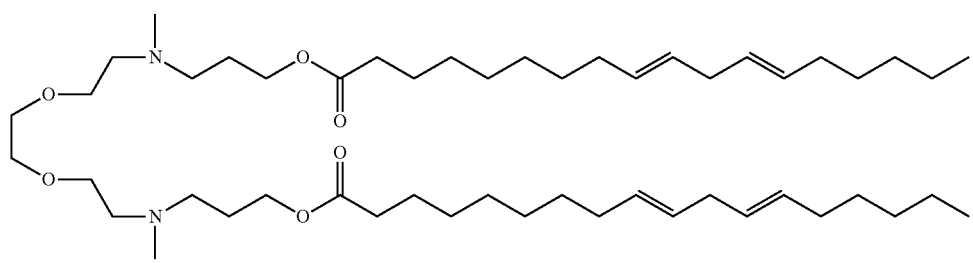
(2-10)

-continued

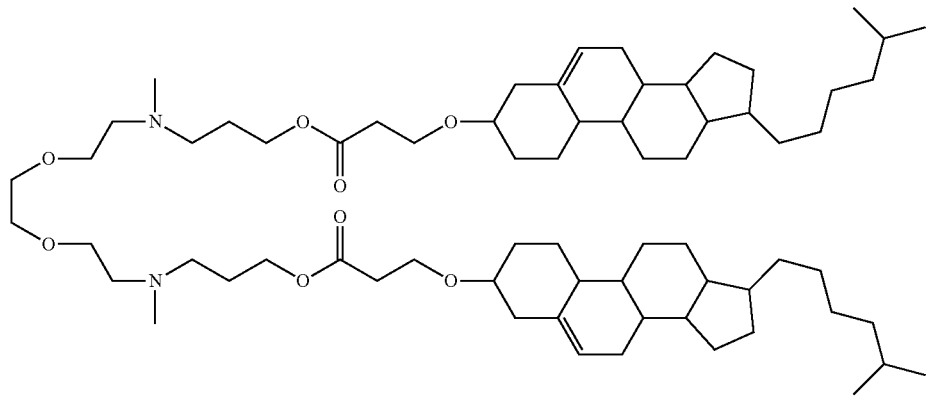

(2-11)

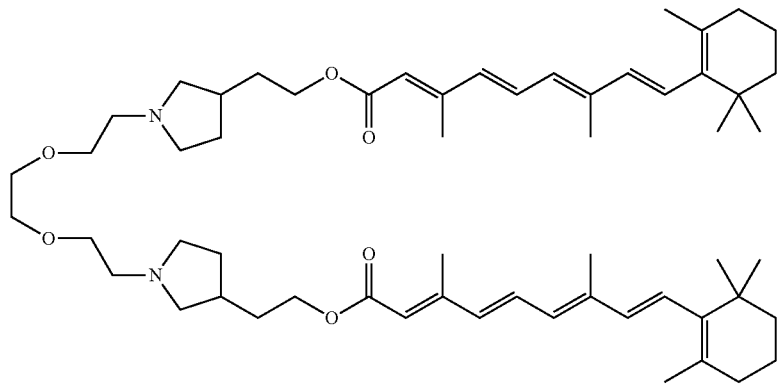

(2-12)

When the lipid particle 1 containing the first and second lipid compound described above is used, the encapsulated amount of nucleic acid is increased and also the nucleic acid introduction ratio can be raised. Further, the death of the introduced cells can be decreased. It is especially preferable to use the compound of Formula (1-01), Formula (1-02) and/or Formula (2-01) because of their particularly high encapsulated amount of the nucleic acid and superior nucleic acid introduction efficiency.

It is preferable that the first and second lipid compounds are contained at approximately 20% to approximately 70% (in molar ratio) to the entire lipid particle 1.

It is also preferable that the lipid particle 1 further contains a lipid which inhibits aggregation of the lipid particle 1, for example, a PEG-modified lipid, particularly, polyethylene glycol (PEG) dimyristoyl glycerol (DMG-PEG), polyamide oligomer induced from omega-amino (oligoethylene glycol) alkanoic acid monomer (U.S. Pat. No. 6,320,017 B1) or monosialoganglioside. It is preferable that such a lipid be contained at approximately 1% to approximately 5% (in molar ratio) to the entire lipid particle 1.

The lipid particle 1 may contain a relatively low toxic lipid for adjusting toxicity, a lipid containing a functional group which couples a ligand to the lipid particle 1, and/or a lipid for inhibiting leakage of a content such as a sterol, for example, cholesterol. It is preferable to contain, in particular, cholesterol.

The type and composition of the lipid to be used for the lipid particle 1 are appropriately selected in consideration of the acid dissociation constant (pKa) of the target lipid particle 1 or the size of the lipid particle 1, the type of the encapsulated substances, the stability in the cell to be introduced or the like. The acid dissociation constant (pKa) should preferably be 6.5 to 8.0. With this value, the efficiency of introduction of nucleic acid to cells can be raised.

For example, it is preferable that the lipid particle 1 contain a compound of Formula (1-01) or Formula (1-02) and/or a compound of Formula (2-01), DOPE and/or DOTAP, cholesterol, and DMG-PEG because of its particularly high encapsulated nucleic acid amount and superior nucleic acid introduction efficiency. For example, it is preferable to contain these components in either one of compositions (1) to (17) listed in Table 1 below.

TABLE 1

| Number | FFT10 | FFT20 | SST04 | DOTAP | DOPE | Cholesterol | PEG-DMG |
|---|---|---|---|---|---|---|---|
| 1 | 74 | 0 | 0 | 21 | 0 | 60 | 4 |
| 2 | 37 | 0 | 7.5 | 21 | 0 | 60 | 4 |
| 3 | 0 | 0 | 0 | 21 | 0 | 30 | 2 |
| 4 | 37 | 0 | 0 | 10.5 | 5.25 | 15 | 1 |
| 5 | 37 | 0 | 0 | 5.25 | 5.25 | 30 | 2 |
| 6 | 37 | 0 | 0 | 10.5 | 5.25 | 60 | 4 |
| 7 | 18.5 | 0 | 0 | 10.5 | 0 | 30 | 2 |
| 8 | 74 | 0 | 0 | 10.5 | 5.25 | 30 | 2 |
| 9 | 37 | 0 | 0 | 10.5 | 5.25 | 30 | 2 |
| 10 | 37 | 0 | 0 | 10.5 | 10.5 | 30 | 2 |
| 11 | 18.5 | 0 | 0 | 21 | 0 | 60 | 4 |
| 12 | 37 | 0 | 0 | 42 | 0 | 30 | 2 |
| 13 | 18.5 | 0 | 0 | 42 | 0 | 30 | 2 |
| 14 | 37 | 0 | 0 | 21 | 0 | 30 | 2 |
| 15 | 37 | 0 | 0 | 0 | 21 | 30 | 2 |
| 16 | 37 | 0 | 0 | 5.25 | 10.5 | 60 | 4 |
| 17 | 0 | 37 | 0 | 10.5 | 5.25 | 60 | 4 |

(Unit: Molar ratio)

With use of the composition (1) in particular, the nucleic acid introduction efficiency can be further raised. The compositions (5) to (8) can adjust the acid dissociation constant of the lipid particle 1 to 6.5 to 8.0 and thus they can further raise the nucleic acid introduction efficiency.

(Nucleic Acid)

The first nucleic acid 2 and the second nucleic acid 3 each are, for example, a single-strand or double strand, cyclic, linear or branched nucleic acid. The first nucleic acid 2 and the second nucleic acid 3 each are, for example, DNA, RNA, PNA or a derivative of any of these. A derivative is a DNA, RNA or PNA, to which a nucleotide analog has been inserted, or DNA, RNA or PNA, whose one end has been modified with a marker or a functional group. For example, the first nucleic acid 2 and the second nucleic acid 3 may be different types of nucleic acids from each other. For example, either one of the first nucleic acid 2 and the second nucleic acid 3 may be DNA, whereas the other may be RNA.

When the first nucleic acid 2 and/or the second nucleic acid 3 is RNA, it is preferable to be modified to have anti-degradation property. Here the modification may be, for example, a well-known modification which can prevent RNA from being degraded by RNase. Such a modification is, for example, use/introduction of a naturally modified nucleotide or a unnatural nucleotide to RNA, use/addition of an unnatural sequence, addition of a natural/unnatural CAP structure or the like.

The naturally modified nucleotide is, for example, pseudo-uridine, 5-methyl cytidine, 1-methyl adenosine, or the like. The unnatural nucleotide is, for example, bridged nucleic acid (BNA), locked nucleic acid (LNA), peptide nucleic acid (PNA), or the like.

The unnatural sequence is, for example, an artificially produced base sequence, which does not exist in nature, for example, a random base sequence, a hybrid sequence of natural/unnatural amino acid and nucleic acid or the like. It is preferable that the unnatural sequence be added, for example, to an end of RNA.

The natural CAP structure is, for example, CAP0 (m7GpppN), CAP1 (m7GpppNm) or the like. The unnatural CAP structure is, for example, anti-reverse cap analog (ARCA), LNA-guanosine or the like. It is preferable that the unnatural CAP structure be added to, for example, a 5' end of RNA.

The first nucleic acid 2 contains a CAR gene sequence 2a. The CAR gene may be the gene of a fusion protein which contains at least an antigen binding domain (extracellular domain) of an antibody bound with a specific target (antigen) and a signal domain (intracellular signal domain) to transmit a signal to activate a T cell by bonding of the target to the antigen binding domain. As the CAR gene, the gene of a fusion protein generally known as CAR may be used, or the gene of a fusion protein obtained by modifying the fusion protein in such a range to exhibit a similar function, a fusion protein to which a further domain is added, or a novel fusion protein having a similar function or the like can be used.

An example of CAR will be described in detail. The CAR contains, for example, an extracellular domain, a transmembrane domain and an intracellular domain.

(a) Extracellular Domains

An extracellular domain is a domain disposed outside of a T cell and to be specifically bound with a target as described above. The extracellular domains contain, for example, an antigen-binding fragment of an anti-target monoclonal antibody, that is, for example, scFv fragment. As the monoclonal antibody, for example, antibodies of rodents (mouse, rat, rabbit, and the like), human antibody or a humanized antibody, and the like can be used. The scFv fragmentation has a structure that a light chain variable region (VL) and a heavy chain variable region (VH) of immunoglobulin are jointed together via a linker. A usable example of the linker is a peptide linker comprising peptides in which amino acids are connected together, for example, into a linear chain form. The peptide linker is, for example, a linker comprising glycine and serine (that is, for example, a GGS linker or GS linker). For example, linkers with 5 amino acid residues can be used.

The type and structure of extracellular domains is selected depending on the type of the target. The target is typically an antigen associated with tumor cells. The antigen associated with tumor cells is, for example, an antigen which is recognized to exhibit specific or selective expression in a tumor cell, a cell of the tissue surrounding the tumor cell, or a living body having the tumor cell. The tumor discussed here is, for example, a B-cell lymphoma, multiple myeloma, retinoblastoma, a pulmonary vacuole tumor, a central nerve tumor or the like. The target, here, is, for example, CD19 antigen, CD20 antigen, GD2 antigen, CD22 antigen, CD30 antigen, CD33 antigen, CD44variant7/8 antigen, CEA antigen, Her2/neu antigen, MUC1 antigen, MUC4 antigen, MUC6 antigen, IL-13receptor-alpha2, immunoglobulin light chain, PSMA antigen, VEGFreceptor2 or the like.

When the target is a leukemia stem cell of marrow system tumor, leukemia precursor cell, leukemic cell or the like, a ligand of polymorph monocyte colony stimulating factor (GM-CSF) receptor, that is, GM-CSF can be used as an extracellular domain.

(b) Transmembrane Domains

A transmembrane domain is a domain provided between an extracellular domain and an intracellular signal domain and disposed in a cell membrane of a T cell. Usable examples of the transmembrane domain are CD28, CD3ε, CD8α, CD3, CD4 and 4-1BB. Or a transmembrane domain made of an artificially constructed polypeptide can be used as well.

(c) Intracellular Signal Domains

An intracellular signal domain is a domain which transmits signals necessary for activation of an T cell when disposed inside of the T cell and an extracellular domain is coupled with an antigen of the target as described above. The intracellular signal domains contain, for example, a domain to transmit signals through TCR complexes (a first domain) and a domain to transmit signals through costimulatory signals (a second domain). As the first domain, CD3ζ, FcεRIγ or the like can be used. Preferably, CD3ζ is used. As the second domain, for example, intracellular domains of costimulatory molecules such as CD28, 4-1BB (CD137), CD2, CD4, CD5, CD134, OX-40, ICOS or the like can be used. Preferably, CD28 or 4-1BB is used. Each of the first domain and the second domain may contain one of the above-listed elements or may take such a structure that the same or different types elements of those listed above are coupled into a tandem form.

The order of coupling of the first domain and the second domain is not particularly limited, but it is preferable that the second domain be disposed on a transmembrane domain side. The first domain and the second domain may be coupled directly with each other or via a linker interposed therebetween. Usable examples of the linker are peptide linkers made of peptides in which 2 amino acids are coupled with each other into a linear chain form.

(d) Other Elements

CAR may contain some other element. As the other element, for example, a leader sequence (signal peptide) promoting secretion of CAR, a leader sequence of the GM-CSF receptor or the like can be used. A spacer domain may be placed between an extracellular domain and a transmembrane domain. The spacer domain can promote bonding between CAR and the target. As the spacer domain, for example, a Fc fragment of human IgG (for example, human IgG1 or human IgG4) can be used. Or, a part of the extracellular domain of CD28 or a part of the extracellular domain of CD8α, or the like can be used as the spacer domain. Note that the spacer domain can be provided also between a transmembrane domain and an intracellular signal domain.

The CAR gene is, for example, that in which genes corresponding to the above-described domains are coupled with each other in an appropriate order. A CAR gene sequence 2a may be that contain any of the above-described CAR genes in its entire length or partially.

It is preferable that the first nucleic acid 2 be DNA.

Figure 2:
FIG. 2 is a diagram showing an example of the first nucleic acid of the embodiment.

The first nucleic acid 2 may contain, for example, a first transposase recognition sequence and a second transposase recognition sequence placed at respective ends of the CAR gene sequence 2a as shown in FIG. 2.

The first transposase recognition sequence 2b and the second transposase recognition sequence 2c are sequences to be recognized by transposases, to which the transposases bind and by which the CAR gene sequence 2a is cut out. The first transposase recognition sequence 2b and the second transposase recognition sequence 2c are base sequences containing the same sequences but inverse to each other. These sequences are sequences also referred to inverted repeat sequences (IRs).

The sequences of the first transposase recognition sequence 2b and the second transposase recognition sequence 2c are selected in response to the type of a transposase gene sequence 3a contained in the second nucleic acid 3.

When the gene of piggyBac is used as the transposase gene sequence 3a, for example, a sequence of SEQ ID 1 shown in Table 2 can be used as the sequence of the CAR gene sequence 2a interposed between the first transposase recognition sequence 2b and the second transposase recognition sequence 2c. Note that the 1st to 312th bases of the SEQ ID 1 are the first transposase recognition sequence 2b (5' IR sequence), the 4300th to 4536th bases are the second transposase recognition sequence 2c (3' IR sequence) and a CAR gene is contained therebetween.

TABLE 2

| Transposase recognition sequence + CAR gene + Transposase recognition sequence (SEQ: ID 1) | | | | | |
|---|---|---|---|---|---|
| tttaacccta | gaaagatagt | ctgcgtaaaa | ttgacgcatg | cattcttgaa | atattgctct | 60 |
| ctctttctaa | atagcgcgaa | tccgtcgctg | tgcatttagg | acatctcagt | cgccgcttgg | 120 |
| agctcccgtg | aggcgtgctt | gtcaatgcgg | taagtgtcac | tgattttgaa | ctataacgac | 180 |
| cgcgtgagtc | aaaatgacgc | atgattatct | tttacgtgac | ttttaagatt | taactcatac | 240 |
| gataattata | ttgttatttc | atgttctact | tacgtgataa | cttattatat | atatattttc | 300 |
| ttgttataga | taagatcttc | aatattggcc | attagccata | ttattcattg | gttatatagc | 360 |
| ataaatcaat | attggctatt | ggccattgca | tacgttgtat | ctatatcata | atatgtacat | 420 |
| ttatattggc | tcatgtccaa | tatgaccgcc | atgttggcat | tgattattga | ctagttatta | 480 |
| atagtaatca | attacggggt | cattagttca | tagcccatat | atggagttcc | gcgttacata | 540 |
| acttacggta | aatggcccgc | ctggctgacc | gcccaacgac | ccccgcccat | tgacgtcaat | 600 |
| aatgacgtat | gttcccatag | taacgccaat | agggactttc | cattgacgtc | aatgggtgga | 660 |
| gtatttacgg | taaactgccc | acttggcagt | acatcaagtg | tatcatatgc | caagtccgcc | 720 |
| ccctattgac | gtcaatgacg | gtaaatggcc | cgcctggcat | tatgcccagt | acatgacctt | 780 |
| acgggacttt | cctacttggc | agtacatcta | cgtattagtc | atcgctatta | ccatggtgat | 840 |
| gcggttttgg | cagtacacca | atgggcgtgg | atagcggttt | gactcacggg | gatttccaag | 900 |
| tctccacccc | attgacgtca | atgggagttt | gttttggcac | caaaatcaac | gggactttcc | 960 |
| aaaatgtcgt | aacaactgcg | atcgcccgcc | ccgttgacgc | aaatgggcgg | taggcgtgta | 1020 |
| cggtgggagg | tctatataag | cagagctcgt | ttagtgaacc | gtcagatcac | tagaagcttt | 1080 |
| attgcggtag | tttatcacag | ttaaattgct | aacgcagtca | gtgcttctga | cacaacagtc | 1140 |
| tcgaacttaa | gctgcagtga | ctctcttaag | gtagccttgc | agaagttggt | cgtgaggcac | 1200 |
| tgggcaggta | agtatcaagg | ttacaagaca | ggtttaagga | gaccaataga | aactgggctt | 1260 |
| gtcgagacag | agaagactct | tgcgtttctg | ataggcacct | attggtctta | ctgacatcca | 1320 |
| ctttgccttt | ctctccacag | gtgtccactc | ccagttcaat | tacagctctt | aaggtcagag | 1380 |

TABLE 2-continued

Transposase recognition sequence + CAR gene +
Transposase recognition sequence (SEQ: ID 1)

```
tacttaatac gactcactat aggctagcct cgagctcaag cttcgaattc gaatggccat 1440
ggagtttggg ctgagctggc ttttcttgt ggctatttta aaaggtgtcc agtgctctag 1500
agacatccag atgacacaga ctacatcctc cctgtctgcc tctctgggag acagagtcac 1560
catcagttgc agggcaagtc aggacattag taaatattta aattggtatc agcaaaaacc 1620
agatggaact gttaaactcc tgatctacca tacatcaaga ttacactcag gagtcccatc 1680
aaggttcagt ggcagtgggt ctggaacaga ttattctctc accattagca acctggagca 1740
agaagatatt gccacttact tttgccaaca gggtaatacg cttccgtaca cgttcggagg 1800
ggggaccaag ctggagctga aacgtggtgg tggtggttct ggtggtggtg gttctggtaa 1860
gcctatccct aaccctctcc tcggtctcga ttctacgggc ggcggcggct ccggtggtgg 1920
tggatccgag gtgcagctgc agcagtctgg acctggcctg gtggcgccct cacagagcct 1980
gtccgtcaca tgcactgtct caggggtctc attacccgac tatggtgtaa gctggattcg 2040
ccagcctcca cgaaagggtc tggagtggct gggagtaata tggggtagtg aaaccacata 2100
ctataattca gctctcaaat ccagactgac catcatcaag acaactcca agagccaagt 2160 tttcttaaaa atgaacagtc tgcaaactga tgacacagcc atttactact gtgccaaaca 2220
ttattactac ggtggtagct atgctatgga ctactggggc caagggacca cggtcaccgt 2280
ctcctcgtac gtcaccgtct cttcacagga tcccgccgag cccaaatctc tgacaaaaac 2340
tcacacatgc ccaccgtgcc cagcacctga actcctgggg ggaccgtcag tcttcctctt 2400
ccccccaaaa cccaaggaca cctcatgat ctcccggacc cctgaggtca catgcgtggt 2460
ggtggacgtg agccacgaag accctgaggt caagttcaac tggtacgtgg acggcgtgga 2520
ggtgcataat gccaagacaa agccgcggga ggagcagtac aacagcacgt accgtgtggt 2580
cagcgtcctc accgtcctgc accaggactg gctgaatggc aaggagtaca agtgcaaggt 2640
ctccaacaaa gccctcccag cccccatcga gaaaaccatc tccaaagcca agggcagcc 2700 ccgagaacca caggtgtaca ccctgccccc atcccgggat gagctgacca agaaccaggt 2760
cagcctgacc tgcctggtca aaggcttcta tcccagcgac atcgccgtgg agtgggagag 2820
caatgggcaa ccggagaaca actacaagac cacgcctccc gtgctggact ccgacggctc 2880
cttcttcctc tacagcaagc tcaccgtgga caagagcagg tggcagcagg ggaacgtctt 2940
ctcatgctcc gtgatgcatg aggctctgca caaccactac acgcagaaga gcctctccct 3000
gtctccgggt aaaaaagatc caaattttg ggtgctggtg gtggttggtg gagtcctggc 3060
ttgctatagc ttgctagtaa cagtggcctt tattatttc tgggtgagga gtaagaggag 3120
caggctcctg cacagtgact acatgaacat gactccccgc cgccccgggc ccacccgcaa 3180
gcattaccag ccctatgccc caccacgcga cttcgcagcc tatcgctcca gagtgaagtt 3240
cagcaggagc gcagacgccc ccgcgtacca gcagggccag aaccagctct ataacgagct 3300
caatctagga cgaagagagg agtacgatgt tttggacaag agacgtggcc gggaccctga 3360
gatgggggga aagccgagaa ggaagaaccc tcaggaaggc ctgtacaatg aactgcagaa 3420
agataagatg gcggaggcct acagtgagat tgggatgaaa ggcgagcgcc ggaggggcaa 3480
ggggcacgat ggcctttacc agggtctcag tacagccacc aaggacacct acgacgccct 3540
tcacatgcag gccctgcctc ctcgctaagc atgctagcta tagttctaga ggtaccggtt 3600
gttaacgtta gccggctacg tatactccgg aatattaata ggcctaggat gcatatggcg 3660
```

TABLE 2-continued

Transposase recognition sequence + CAR gene +
Transposase recognition sequence (SEQ: ID 1)

```
gccgcttccc tttagtgagg gttaatgctt cgagcagaca tgataagata cattgatgag 3720
tttggacaaa ccacaactag aatgcagtga aaaaaatgct ttatttgtga aatttgtgat 3780
gctattgctt tatttgtaac cattataagc tgcaataaac aagttaacaa caacaattgc 3840
attcatttta tgtttcaggt tcagggggag atgtgggagg ttttttaaag caagtaaaac 3900
ctctacaaat gtggtaaaat ccgataagga tcgatccggg ctggcgtaat agcgaagagg 3960
cccgcaccga tcgccttcc caacagttgc gcagcctgaa tggcgaatgg acgcgccctg 4020
tagcggcgca ttaagcgcgg cgggtgtggt ggttacgcgc agcgtgaccg ctacacttgc 4080 cagcgccta gcgcccgctc ctttcgcttt cttcccttcc tttctcgcca cgttcgcccg 4140
atagcgataa ggatccgcgt atggtgcact ctcagtacaa tctgctctga tgccgcatag 4200
ttaagccagc cccgacaccc gccaacaccc gctgacgcgc cctgacgggc ttgtctgctc 4260
ccggcatccg cttacagaca agctgtgacc gtctccggga ttttgttact ttatagaaga 4320
aattttgagt ttttgttttt ttttaataaa taaataaaca taaataaatt gtttgttgaa 4380
tttattatta gtatgtaagt gtaaatataa taaaacttaa tatctattca aattaataaa 4440
taaacctcga tatacagacc gataaaacac atgcgtcaat tttacgcatg attatcttta 4500
acgtacgtca caatatgatt atctttctag ggttaa                            4536
```

The length of the first nucleic acid 2 is, for example, 3 to approximately 20,000 bases. It is preferable that 1 to 100 molecules of the first nucleic acid 2 are encapsulated in the nucleic acid-introducing carrier 10.

The second nucleic acid 3 contains the transposase gene sequence 3a. As the transposase gene sequence, for example, a sequence encoding a gene of, for example, piggyBac, Sleeping Beauty, Frog Prince, Hsma, Minos, Tol1, Tol2, Passport, hAT, Ac/Ds, PIF, Harbinger, Harbinger3-DR, Himar1, Hermes, Tc3, Mos1 or the like can be used. The second nucleic acid 3 may be DNA or RNA, but preferably RNA. In the case of RNA, the second nucleic acid 3 may be mRNA of the transposase gene.

As the transposase gene sequence 3a, for example, the following sequences can be used. Table 3 shows sequences of DNA, but in the case of RNA, those of the following sequence, in which thymine (T) is substituted by uracil (U) may be used.

TABLE 3

PiggyBac gene (SEQ: ID 2)

```
aatgggtagt tctttagacg atgagcatat cctctctgct cttctgcaaa gcgatgacga  60
gcttgttggt gaggattctg acagtgaaat atcagatcac gtaagtgaag atgacgtcca 120
gagcgataca gaagaagcgt ttatagatga ggtacatgaa gtgcagccaa cgtcaagcgg 180
tagtgaaata ttagacgaac aaaatgttat tgaacaacca ggttcttcat tggcttctaa 240
cagaatcttg accttgccac agaggactat tagaggtaag aataaacatt gttggtcaac 300
ttcaaagtcc acgaggcgta gccgagtctc tgcactgaac attgtcagat ctcaaagagg 360
tccgacgcgt atgtgccgca atatatatga cccacttta tgcttcaaac tattttttac 420
tgatgagata atttcggaaa ttgtaaaatg gacaaatgct gagatatcat tgaaacgtcg 480
ggaatctatg acaggtgcta catttcgtga cacgaatgaa gatgaaatct atgctttctt 540
tggtattctg gtaatgacag cagtgagaaa agataaccac atgtccacag atgacctctt 600
tgatcgatct ttgtcaatgg tgtacgtctc tgtaatgagt cgtgatcgtt ttgatttttt 660
gatacgatgt cttagaatgg atgacaaaag tatacggccc acacttcgag aaaacgatgt 720
atttactcct gttagaaaaa tatgggatct ctttatccat cagtgcatac aaaattacac 780 tccagggcc cattgtgacca tagatgaaca gttacttggt tttagaggac ggtgtccgtt 840
taggatgtat atcccaaaca agccaagtaa gtatggaata aaaatcctca tgatgtgtga 900
```

TABLE 3-continued

PiggyBac gene (SEQ: ID 2)

```
cagtggtacg aagtatatga taaatggaat gccttatttg ggaagaggaa cacagaccaa  960
cggagtacca ctcggtgaat actacgtgaa ggagttatca aagcctgtgc acggtagttg 1020
tcgtaatatt acgtgtgaca attggttcac ctcaatccct ttggcaaaaa acttactaca 1080
agaaccgtat aagttaacca ttgtgggaac cgtgcgatca aacaaacgcg agataccgga 1140
agtactgaaa aacagtcgct ccaggccagt gggaacatcg atgttttgtt ttgacggacc 1200
ccttactctc gtctcatata aaccgaagcc agctaagatg gtatacttat tatcatcttg 1260
tgatgaggat gcttctatca acgaaagtac cggtaaaccg caaatggtta tgtattataa 1320
tcaaactaaa ggcggagtgg acacgctaga ccaaatgtgt tctgtgatga cctgcagtag 1380
gaagacgaat aggtggccta tggcattatt gtacggaata ataaacattg cctgcataaa 1440
ttctttattt atatacagcc ataatgtcag tagcaaggga gaaaaggttc aaagtcgcaa 1500
aaaatttatg agaaacettt acatgagcct gacgtcatcg tttatgcgta agcgtttaga 1560
agctcctact ttgaagagat atttgcgcga taatatctct aatattttgc caaatgaagt 1620
gcctggtaca tcagatgaca gtactgaaga gccagtaatg aaaaaacgta cttactgtac 1680
ttactgcccc tctaaaataa ggcgaaaggc aaatgcatcg tgcaaaaaat gcaaaaaagt 1740
tatttgtcga gagcataata ttgatatgtg ccaaagttgt ttctg              1785
```

The second nucleic acid 3 may have a further sequence in addition to the transposase gene sequence 3a. The further sequence is, for example, 5' end leader sequence, Internal Ribosome Entry Site (IRES), a transcription termination sequence, Poly(A) sequence or the like. The second nucleic acid 3 may have a 5'-cap structure.

The length of the second nucleic acid 3 is, for example, from approximately 20 to approximately 5,000 bases. It is preferable for the second nucleic acid 3 to contain 1 to approximately 1,000 molecules in its nucleic acid-introducing carrier 10.

The nucleic acid encapsulated in the lipid particle 1 may contain a further nucleic acid in addition to the first nucleic acid 2 and the second nucleic acid 3. Such a nucleic acid is, for example, DNA or RNA having a function of modifying DNA, that is, for example, methylation, demethylation, or recovering and/or bonding of DNA or the like. These nucleic acids may be, for example, DNA or RNA coding for a protein having activity of modification described above. With these nucleic acids contained, the above-described modification can be added to the CAR gene sequence 2a introduced into a genome or the sequence located in the vicinity. Thus, for example, a further functional modification can be added to T cells.

(Nucleic Acid Condensation Peptide)

A nucleic acid condensation peptide 5 is a peptide which condenses more nucleic acids into smaller size and efficiently encapsulate a great number of nucleic acids in the lipid particle 1. As preferable examples of such a peptide are cationic peptides. A cationic peptide enters gaps between spiral shapes of anionic nucleic acids to reduce the gaps, thus making it possible to condense nucleic acids.

A preferable nucleic acid condensation peptide 5 is, for example, a peptide containing cationic amino acids at a ratio of 45% or more of its entirety. A more preferable nucleic acid condensation peptide 5 includes RRRRRR (the first amino acid sequence) at one end, and the other end has sequence RQROR (the second amino acid sequence). Between the both amino acid sequences, none or one or more middle sequence consisting of RRRRRR or ROROR is contained. Of the first amino acid sequence, the second amino acid sequence and the middle sequence, two or more neutral amino acids are contained between two sequences adjacent to each other. The neutral amino acid is, for example, G or Y.

The nucleic acid condensation peptide 5 preferably includes the following amino acid sequences.

RORORYYRORORGGRRRRRR (SEQ ID: 3)
RQRQRGGRRRRRR (SEQ ID: 4).

With such nucleic acid condensation peptide 5, cationicity by R can efficiently condense the nucleic acids and weaken the anionicity of the nucleic acid, and therefore the nucleic acids can be efficiently encapsulated in the lipid particle 1. Further, the nucleic acid condensation peptide 5 can efficiently dissociate the nucleic acids in cells, and therefore the nucleic acids introduced in cells can be efficiently expressed in the cells.

Or, the nucleic acid condensation peptide 5 includes RRRRRR (the third amino acid sequence) in one end, and RRRRRR (the fourth amino acid sequence) in the other end. Between the both amino acid sequences, none or one or more middle sequences of RRRRRR or RORQR is contained. Of the third amino acid sequence, the fourth amino acid sequence and the middle sequence, two or more neutral amino acids are contained between two sequence adjacent to each other.

Such a nucleic acid condensation peptide 5 preferably contains the following amino acid sequence.

RRRRRRYYRORQRGGRRRRRR (SEQ ID 5).

Such a nucleic acid condensation peptide 5 has strong cationicity at both ends, and it has a high affinity with nucleic acids. Thus, the nucleic acids can be condensed further efficiently, and more nucleic acids can be encapsulated in the lipid particle 1. As a result, the amount of the nucleic acid remaining outside the lipid particle 1 is reduced, thereby preventing the aggregation between nucleic acid-introducing carriers, and therefore the nucleic acid-introducing carriers can be easily taken into cells.

Further, the nucleic acid condensation peptide 5 containing the following amino acid sequence can be used in combination with any of the nucleic acid condensation peptides 5.

GNQSSNFGPMKGGNFGGRSSGPYGGGGQYFAK-PRNOGGY (M9) (SEQ ID: 6)

This peptide can further condense the nucleic acid complex condensed with the nucleic acid condensation peptide 5. Thus, nucleic acid-introducing carriers of a further smaller particle size can be obtained. Such nucleic acid-introducing carrier can be easily taken into cells, and therefore, more efficiently, the nucleic acid can be introduced into the genome of the cells.

For example, before encapsulated into the lipid particle 1, by agitating and mixing the first nucleic acid 2 and the second nucleic acid 3 with the nucleic acid condensation peptide 5, the first nucleic acid 2 and second nucleic acid 3 can be condensed. The first nucleic acid 2 and the second nucleic acid 3 may be condensed together or separately.

Because of an advantageous effect described above, it is preferable to use the nucleic acid condensation peptide 5, but the nucleic acid condensation peptide 5 may not necessarily be used depending on the type of nucleic acid to use or the condition for culturing cells or the like.

A further ingredient may be encapsulated in the nucleic acid-introducing carrier 10 in addition to the nucleic acids described above. For example, a compound regulating the expression of the nucleic acid in cells, such as retinoic acid, cyclic adenosine monophosphate (CAMP) or ascorbic acid or the like, peptide, polypeptide, cytokine, a growth factor, an apoptotic factor, a differentiation inducer, other cell surface receptor, ligands thereof or the like can be contained.

The nucleic acid-introducing carrier 10 can be produced by using, for example, a well-known method used to enclose small molecules into lipid particles or the like, such as the van gum method, organic solvent sampling method, surfactant removal method, freeze thaw method or the like. A nucleic acid-introducing carrier can be prepared by, for example, such a procedure that includes adding aqueous buffer solution containing ingredients to be encapsulated, such as the first nucleic acid 2, the second nucleic acid 3 and the like to a mixture obtained by containing the material of the lipid particle 1 in an organic solvent such as an alcohol, followed by stirring and suspending. The quantitative ratio of the nucleic acids encapsulated in the lipid particle 1 can be adjusted easily by changing the quantitative ratio between both of these in the aqueous buffer solution. The encapsulated amount of the nucleic acids can be confirmed by, for example, using commercially available a DNA and RNA quantification kit or the like.

The average particle diameter of the nucleic acid-introducing carrier 10 is, for example, approximately 50 nm to approximately 300 nm, and preferably approximately 50 nm to approximately 200 nm. The particle diameter can be reduced by, for example, an ultrasonic treatment. The size of the nucleic acid-introducing carrier 10 can be adjusted by permeating it through a polycarbonate membrane or a ceramic membrane. Note that the average particle diameter of the nucleic acid-introducing carrier 10 can be measured, for example, by a zeta sizer using the dynamic light scattering method.

In a further embodiment, the first nucleic acid 2 and the second nucleic acid 3 may have a core-shell structure.

Figure 3:
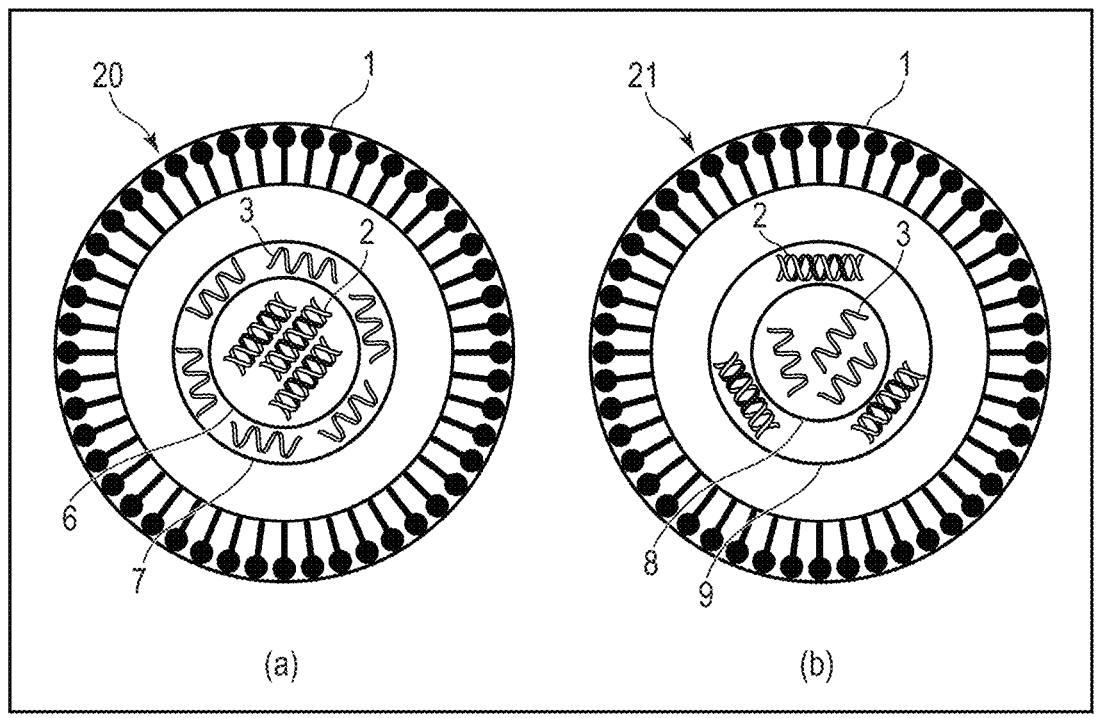
FIG. 3 is a cross section showing an example of the nucleic acid-introducing carrier of the embodiment.

The nucleic acid-introducing carrier 20 shown in FIG. 3, part (a) has a core-shell structure including a first nucleic acid core 6 containing the first nucleic acid 2 and a second nucleic acid shell 7 containing the second nucleic acid 3 which coats the first nucleic acid core 6. On the other hand, the nucleic acid-introducing carrier 21 shown in FIG. 3, part (b) has a core-shell structure including a second nucleic acid core 8 containing the second nucleic acid 3 and a first nucleic acid shell 9 containing the first nucleic acid 2 which coats the second nucleic acid core 8. The core-shell structure is encapsulated in the lipid particle 1.

The core-shell structure can be prepared, for example, as follows. First, a nucleic acid for the core is condensed with the nucleic acid condensation peptide 5, and thus a core is produced. Then, a nucleic acid for the shell is brought into contact with the core, and thus the nucleic acid for the shell electrostatically attaches around the core, and thus the shell is formed. The nucleic acid for the shell may be obtained by being condensed with the nucleic acid condensation peptide 5. As a result, a core-shell structure is formed. Then, the core-shell structure is added to a solvent containing the material of the lipid particle 1, followed by stirring, and thus the core-shell structure is encapsulated in the lipid particle 1 and the nucleic acid-introducing carrier 20 or 21 is prepared.

With such a structure, the first nucleic acid 2 and the second nucleic acid 3 can be introduced at different timings. The release speed and the release duration of the nucleic acid contained in the core can be adjusted by the composition or amount of the nucleic acid condensation peptide 5, the amount of the nucleic acid or the like. In the production of CAR-T cells, since the transposase protein translated from the second nucleic acid 3 acts on the first nucleic acid 2, it is preferable that the nucleic acid-introducing carrier has the configuration of nucleic acid-introducing carrier 20 which releases the second nucleic acid 3 earlier.

Figure 4:
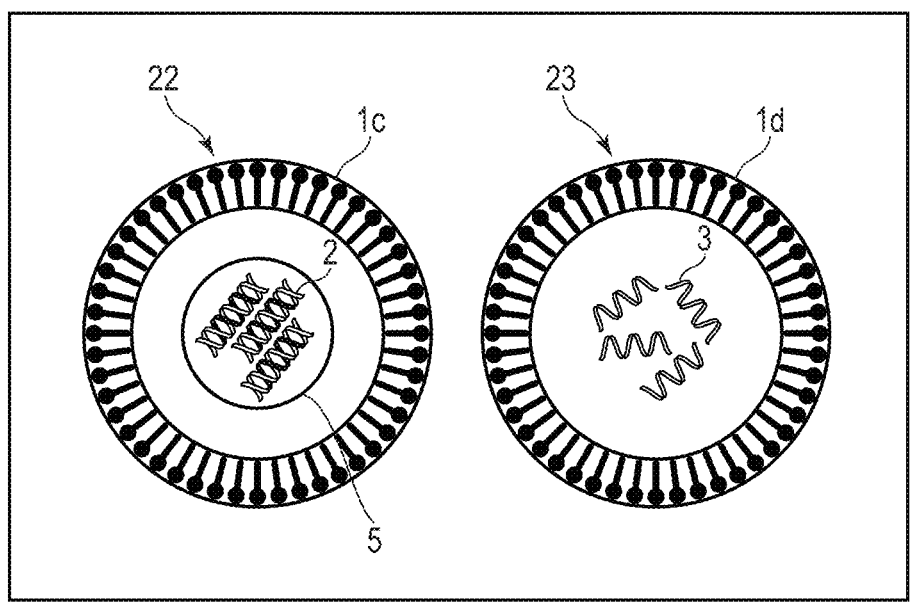
FIG. 4 is a cross section showing another example of the nucleic acid-introducing carrier of the embodiment.

According to the further embodiment, as shown in FIG. 4, the first nucleic acid 2 and the second nucleic acid 3 may be encapsulated to separate lipid particles 1. That is, the first nucleic acid 2 is contained in a first lipid particle 1c (the first sub-nucleic acid-introducing carrier 22), and the second nucleic acid 3 is contained in a second lipid particle 1d (the second sub-nucleic acid-introducing carrier 23). The first nucleic acid 2 and the second nucleic acid 3 each may be contained in the respective lipid particle in the state that they are condensed with the nucleic acid condensation peptide 5.

The first lipid particle 1c and the second lipid particle 1d may have the same composition with each other or different compositions from each other.

With the first sub-nucleic acid-introducing carrier 22 and the second sub-nucleic acid-introducing carrier 23, the first nucleic acid 2 and the second nucleic acid 3 can be introduced at different timings with an interval longer than that for the case of the nucleic acid-introducing carriers 20 and 21, which have the core-shell structure. For example, in a gene introduction step (S2), which will be described later, after one carrier is brought into contact, the other can be brought after an interval of 30 minutes or more. Thus, the difference between introduction timings can be more easy adjusted than the case where the nucleic acid-introducing carriers 20 and 21 are used. It is preferable to bring the second sub-nucleic acid-introducing carrier 23 into contact with the cells earlier than the first sub-nucleic acid-introducing carrier 22. Or both may be brought into contact with the cells at the same time.

The nucleic acid-introducing carriers of the embodiment explained above may be provided as a composition contained in an appropriate carrier. The carrier may be, for example, water, a salt solution such as saline, a glycine aqueous solution, a buffer solution or the like.

When the nucleic acid-introducing carrier is of a form such as the first sub-nucleic acid-introducing carrier 22 and the second sub-nucleic acid-introducing carrier 23 shown in the FIG. 4, they may be accommodated in separate containers and provided as separate compositions.

The compositions may further contain a material which improves preservation stability. The material which improves preservation stability is not particularly limited, but examples thereof are glycoproteins such as albumin, lipoprotein, apolipoprotein and globulin; PH regulator, buffering agent, tonicity adjustor; pharmaceutically acceptable participating agents which bring a pharmaceutical formulation close to a physiological condition, such as sodium acetate, sodium lactate, sodium chloride, potassium chloride and calcium chloride, lipophilic free radical quencher which controls damage which may be caused by free radical, such as the α-tocopherol and lipid protecting agents including water-soluble chelators to suppress peroxidative damage of lipids and improve storage stability such as ferrioxamine. The material to improve reservation stability should preferably be added after the formation of the nucleic acid-introducing carriers.

The compositions may be sterilized by a general method. Or, the composition may be provided as a liquid or a powder obtained by drying it. For example, the composition of the powder becomes usable by dissolving it into an appropriate liquid.

The concentration of the nucleic acid-introducing carrier contained in the composition is not particularly limited, but it is 0.01 to 30% by mass, or preferably, 0.05 to 10% by mass. The concentration is selected appropriately according to the object.

—Method of Producing CAR-T Cells

Figure 5:
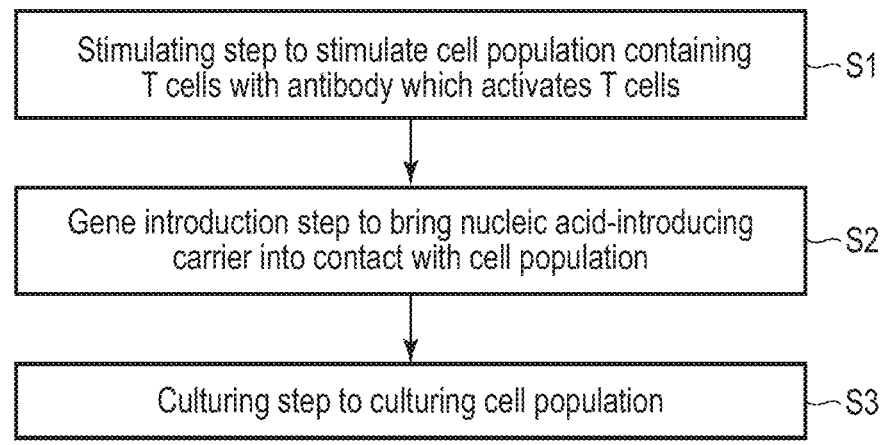
FIG. 5 is a flowchart illustrating an example of the method of producing CAT-T cells of the embodiment.

The method of producing CAR-T cells, using the nucleic acid-introducing carriers of the embodiment will be described below. The method of producing the CAR-T cells of the embodiment comprises the following steps shown in FIG. 5. A stimulating step (S1) which stimulates a cell population containing T cells with an antibody which activates T cells; a gene introduction step (S2) which brings the nucleic acid-introducing carrier of the embodiment into contact with the cell population after the stimulating step, and a culturing step (S3) which cultures the cell population after the gene introduction step.

Hereinafter, each step will be described in detail.

First, prior to the stimulating step (S1), a cell population containing T cells is prepared. The T cells include a CD4$^+$/CD8$^-$ T cell, a CD4$^-$/CD8$^+$ T cell, a T cell prepared from an iPS cells, an αβ-T cell, a γδ-T cell, a precursor cell or the like. As long as such T cells are contained, various cell populations can be used. The cell population should preferably be, for example, peripheral blood mononuclear cells (PBMC) extracted from peripheral blood.

Preferably the cell population is an autologous cell population extracted from an subject to which CAR-T cells are administered, which is obtained as the result of the production method of the embodiment, but a cell population originated from others, commercially available cell population or the like can be also used. Further, such a cell population may be used, that has been subjected to a treatment of isolating unnecessary cells from the extracted or obtained cell population.

Preferably the cell population is, for example, cultured in an appropriate culture medium and culture conditioning. Then, as shown in step (S1) of FIG. 6, an antibody 26 which activates T cells is brought into contact. Thus, the T cells can be stimulated by the antibody 26 (stimulating step (S1)). For the contact with the antibody 26, for example, a method of adding the antibody 26 to a cell suspension liquid, a method of adding beads coated with the antibody 26 to a cell suspension, or a method of adding a cell suspension to, for example, a container whose culture surface is coated with the antibody 26, can be used.

It is preferable to use, for example, at least one of an anti-CD3 antibody and an anti-CD28 antibody as the aforementioned antibody. The anti-CD3 antibody and the anti-CD28 antibody may be used in the form of the entire region of the antibody or a part thereof, for example, F(ab')$_2$ fragment as long as it exhibits binding properties to antigens.

Figure 6:
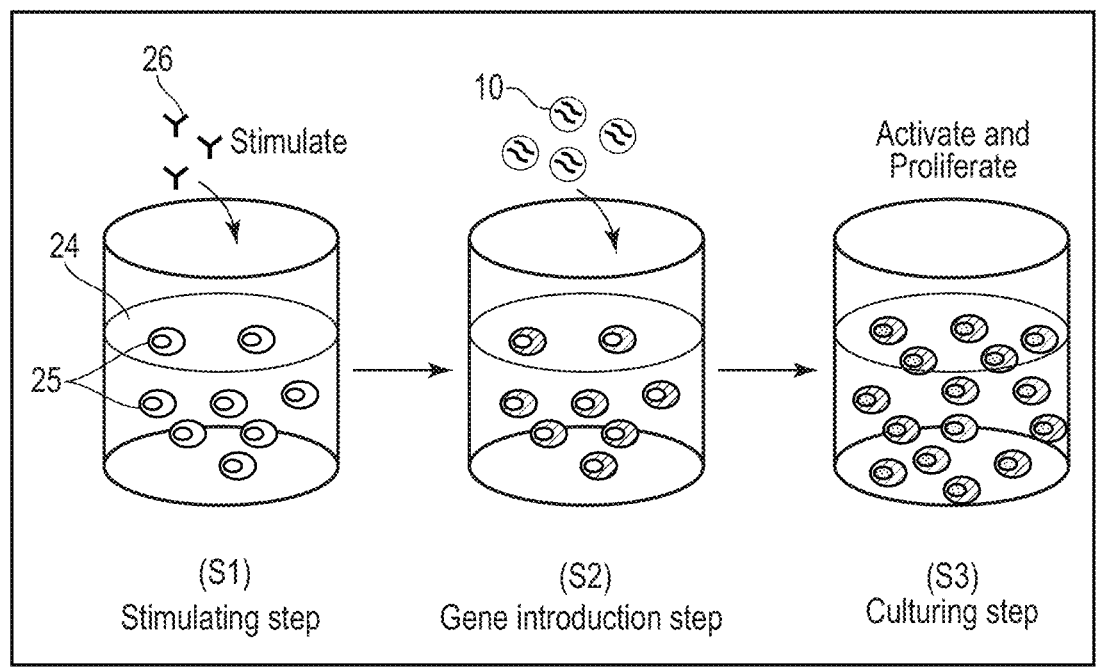
FIG. 6 is a schematic diagram showing an example of the method of producing CAT-T cells of the embodiment.

Then, as shown in step (S2) of FIG. 6, the nucleic acid-introducing carrier 10 is brought into contact with a cell population 25 (gene introduction step (S2)). Here, an example in which a nucleic acid-introducing carrier 10 is used is shown, but the nucleic acid-introducing carriers 20 and 21 or the first sub-nucleic acid-introducing carriers 22 and the second sub-nucleic acid-introducing carriers 23 can be used similarly. The contact can be achieved by adding the nucleic acid-introducing carriers 10 (for example, the form of the composition) to a cell suspension in which cell populations 25 are suspended in the culture medium 24. Or, the contact may be carried out by a method of adding a cell suspension to a container or the like, to a surface of which the nucleic acid-introducing carrier 10 is adhered or immobilized as will be described later.

By the contact of the nucleic acid-introducing carriers 10 in the gene introduction step (S2), the first nucleic acid and the second nucleic acid can be introduced into cells. The introduction is carried out, for example, as follows. First, as the nucleic acid-introducing carriers 10 are contacted, the nucleic acid-introducing carriers 10 are taken into the T cells 25 by endocytosis. From the lipid particles 1 of the nucleic acid-introducing carriers 10 taken into the T cell 25, the first nucleic acid 2 and the second nucleic acid 3 are released within the respective T cell 25. Thereafter, a transposase is translated from the second nucleic acid 3.

The transposase recognizes transposase recognition sequences 2b and 2c of the first nucleic acid 2 and excises out a CAR gene sequence 2a and the transposase recognition sequences 2b and 2c from the first nucleic acid 2. A complex of the excised fragments and the transposase bonds to the genome of the T cell to cut the genome and inserts the CAR gene sequence 2a into the genome of the T cell.

As described above, the CAR gene sequence 2a is introduced on the genome of T cell 25.

Here, when the nucleic acid-introducing carriers 10 contain the second nucleic acid 3 in the form of DNA, transcription and translation are necessary in the stage that transposase is expressed in cells. But when introduced in the form of RNA, the transcription process can be omitted, thereby making it possible to express transposase in cells more quickly and at high efficiency. As a result, the CAR gene sequence 2a can be introduced into the genome of the T cell 25 more effectively.

Then, the obtained cell populations 25 are cultured (culture process (S3) in FIG. 6). The culture period is, for example, 7 to 28 days, preferably 10 to 21 days, or more preferably, 12 to 16 days.

For the basic culture medium to be used for culturing, a commonly used type suitable for culturing T cells may be used. Usable examples of the culture medium are Tex-MACS™, AIM V (registered trademark) and ALys705. The other culturing conditions may be general ones suitable for survival and proliferation of T cells, that is, for example, the temperature and the $CO_2$ concentration may preferably be 37° C. and 5.0%, respectively.

In the culturing step (S3), it is preferable to add a T cell growth factor (for example, IL-15 and/or IL-7) to the culture medium in order to improve the proliferation factor and survival rate of T cells. The amount of addition of IL-15 should preferably be, for example, 5 to 10 ng/ml, and the amount of addition of IL-7 should preferably be, for example, 5 to 10 ng/ml. Serum (a human serum or fetal bovine serum or the like, preferably self-serum) may be added to the culture medium for culturing, but it is preferable to use a serum-free medium.

For example, by the stimulating step (S1), T cells contained in the cell populations 25 are activated and then through the culturing step (S3), the T cells can be proliferated.

After the culture, the cell populations can be cryopreserved. In this case, however, it is preferable to fuse the cell populations when to be used, and carry out the stimulating step (S1) and culturing step (S3) again.

By the above-described processing steps, CAR-T cells can be produced. For example, in a certain embodiment, CAR-T cells can be produced by performing the processing steps (S1) to (S3) even without carrying out other additional procedure or steps.

After the culturing step (S3), for example, the obtained CAR-T cells are collected. The collection can be performed by a general process, for example, pipetting, centrifuging or the like.

According to the nucleic acid-introducing carrier of the embodiment, the first nucleic acid 2 and the second nucleic acid 3 can be introduced in T cells more efficiently and the CAR gene can be introduced into the genomes of the T cells, thereby making it possible to express CAR genes in the cells more efficiently.

For example, the nucleic acid-introducing carrier of the embodiment, unlike the case where lipofection (a complex of lipid and nucleic acid) is used, encapsulates a nucleic acid in a lumen 1b of the lipid particle 1, and thus more nucleic acids are contained and they are protected from decomposition or the flocculation with unnecessary molecules. Therefore, the nucleic acid-introducing carrier of the embodiment is superior in the introduction efficiency of nucleic acid into cells and also superior in the introduction ratio of the introduced CAR gene into genome and the amount of expression of CAR. Further, the ratio in quantity between the first nucleic acid 2 and the second nucleic acid 3 to be introduced can be easily adjusted.

According to the method of producing the CAR-T cells of the embodiment, the nucleic acid-introducing carrier of the embodiment is used, and therefore CAR-T cells of high CAR expressibility can be produced at high efficiency by a simpler operation. Thus, it is not necessary to perform complicated operations in the gene introduction step and the culturing step, and the cost and work can be reduced. Further, it is also possible to prevent the degradation in quality, the production quantity and the like, caused by contamination. As described above, according to the method of the embodiment, CAR-T cells can be produced more efficiently, and thus the production cost can be reduced.

Additionally, according to the nucleic acid-introducing carrier of the embodiment, nucleic acid can be introduced uniformly into cell populations, and therefore the quality of the produced CAR-T cells is stable. Further, the cell population obtained by the production method of the embodiment contains more T cells (CAR-T cells) which express CAR gene. Such a feature is also a factor that the efficiency of production of CAR-T cells by the method of the embodiment is very high.

Moreover, the CAR-T cells contained therein exhibit a higher expressibility of CAR gene than that by a conventional method which uses lipofection. Therefore, when the CAR-T cells prepared by the method of the embodiment are used for CAR-T cellular therapy, the therapeutic effect, for example, the antitumor effect is improved more.

When introducing the transposase gene in the form of RNA, the transposase gene is not integrated on the genome of cells. Therefore, CAR-T cells which prevent the disadvantageous influence caused by transposase gene being integrated in the genome of cells can be produced.

The efficiency of introduction of CAR gene to the genome of the T cells can be raised more by using the nucleic acid condensation peptide 5 for the nucleic acid-introducing carrier 10 as discussed above, by imparting anti-degradability to RNA and by containing the first and/or second lipid compounds in the lipid particle 1. As a result, the efficiency of production of CAR-T cells can be raised.

With use of the CAR-T cells obtained by the method of the embodiment, a cell formulation may be produced. The cell formulation can contain a therapeutically effective quantity of CAR-T cells. The cell formulation may contain a drug which protects CAR-T cells, such as dimethyl sulfoxide (DMSO) or serum albumin, a drug which prevents proliferation of microbes such as an antibiotic, or a drug which prevents activation, proliferation and differentiation induction of cells, such as vitamins, cytokine, growth factor, steroids or the like.

The route of administration of the CAR-T cells or cell formulations in the embodiment is not particularly limited. For example, the administration is done by an intravenous injection, intraarterial injection, intraportal injection, intradermal injection, hypodermic injection, intramuscular injection or intraperitoneal injection. The administration method may be a local administration. In that case, it is injected, for example, directly to a target tissue, organ or organ. The administration schedule should be select in consideration of sex, age, weight, condition or the like of an subject (patient) and it may be a single administration or may be continuous or periodical multiple administrations.

—Kit

A kit of the embodiment is a kit used for the method of production of CAR-T cells and contains the nucleic acid-introducing carrier of the embodiment and a material which improves the reservation stability of the nucleic acid-introducing carrier.

The nucleic acid-introducing carrier can be provided, for example, as a composition as described above. When the nucleic acid-introducing carriers are provided as the first sub-nucleic acid-introducing carrier 22 and the second sub-nucleic acid-introducing carrier 23, the kit may contain either one or both of a composition containing the first including sub-nucleic acid-introducing carrier 22 and a composition containing the second sub-nucleic acid-introducing carrier 23.

Or, a composition which contains the first sub-nucleic acid-introducing carrier 22 but does not contain the second sub-nucleic acid-introducing carrier 23 may be provided. Such a composition may be used to introduce CAR gene into cells when introducing the CAR gene by a method without using transposase.

The material which improves the reservation stability is one of those described above.

The kit may further comprise some other ingredients in the composition or as some other composition. The other component contains an antibody, peptide or the like, which activates a cell culture medium and/or T cells.

In the kit of the embodiment, the nucleic acid-introducing carrier 10 (or the sub-nucleic acid-introducing carriers 20 and 21, or the first nucleic acid-introducing carrier 22 and second sub-nucleic acid-introducing carrier 23) may be directly or indirectly attached or immobilized to one surface of the solid phase, to be provided. The solid phase is, for example, a container of a material, for example, metal, resin, gel or fiber, but not necessarily be of a container shape, and may be plate, sheet or the like.

When such a solid phase is used for the method of production of the CAR-T cells of the embodiment, the gene introduction step (S2) can be simply carried out by adding a cell suspension containing the cell populations 25 on a surface to which the solid-phase nucleic acid-introducing carrier 10 is attached or immobilized. For example, the nucleic acid-introducing carrier 10 is releasably attached or immobilized. Therefore, when a cell suspension is added, the nucleic acid-introducing carrier 10 is released into the cell suspension to be brought into contact with the cell populations 25.

For example, the direct attachment and immobilization can be carried out by directly applying the composition on the surface of the solid phase, followed by drying. For example, the indirect attachment and immobilization can be carried out by applying the composition through, for example, peptide, resin, antibody or the like on the solid phase, followed by drying.

EXAMPLES

Examples in which lipid particle and CAR-T cells are produced by the method of the embodiment and used will be described. However, the embodiments are not limited to the following examples.

Example 1: Evaluation of the Efficiency of Introduction of Lipid Particle Containing Nucleic Acid into PBMC Cells —Preparation of DNA-Encapsulating Carrier As DNA, plasmid DNA in which NanoLuc gene is linked to a downstream of the cytomegalovirus promoter was used. Cationic peptide was added to a DNA solution containing the DNA, thereby forming a DNA-peptide complex. Then, the resultant was added to an ethanol-dissolved lipid solution (((6) FFT10 (lipid compound of Formula (1-01))/DO-TAP/DOPE/cholesterol/PEG-DMG=37/10.5/5.75/60/4 mol) and further 10 mM of HEPES (pH 7.3) was gently added thereto. Thereafter, the resultant was washed and concentrated by centrifuging ultrafiltration and thus a DNA-encapsulating carrier was obtained. The encapsulated DNA amount in the nucleic acid-introducing carrier was measured with Quant-iT (registered trademark) PicoGreen dsDNA Assay Kit (a product of Thermo Fischer Scientific Inc.), and it was confirmed that a sufficient quantity of DNA was encapsulated.

—Preparation of the RNA-Encapsulating Carrier

As RNA, messenger-RNA (mRNA) of a green fluorescent protein (GFP) (a product of OZ Biosciences), which is a reporter gene, was used. An RNA solution containing this mRNA was added to an ethanol-dissolved lipid solution (((6) FFT10/DOTAP/DOPE/cholesterol/PEG-DMG=37/10.5/5.25/60/4 mol), and suspended with pipetting. After that, 10 mM of HEPES (pH 7.3) was added gently, and the solution was washed and concentrated by centrifuging ultrafiltration, thus obtaining an RNA-encapsulating carrier. The encapsulated RNA amount in the nucleic acid-introducing carrier was measured with QuantiFluor (registered trademark) of RNA System (a product of Promega), and it was confirmed that a sufficient quantity of mRNA was encapsulated.

—Preparation of PBMC

Human peripheral blood mononuclear cells (PBMCs) were cultured with a TexMACS culture medium (a product of Miltenyi Biotech), and the cells were collected by centrifuging. Then, the cells were suspended in fresh TexMACS to have a ratio of $3.3 \times 10^6$ cells/mL, and 300 μL of a cell suspension was added to 4-well culture dish (of Matsunami) to make $1.0 \times 10^6$ cells/well.

—Introduction of Nucleic Acid by DNA-Encapsulating Carrier and RNA-Encapsulating Carrier Then, the DNA-encapsulating carrier and the RNA-encapsulating carrier were added to the well to make 2.4 μg/well for each of DNA and RNA, a total of 4.8 μg/well and were cultured at 37° C. in a 5%-$CO_2$ atmosphere.

—Introduction of DNA to Cells by Lipofectamine 3000

As a control for comparison, the plasmid DNA and mRNA were introduced into PBMC by using a reagent, Lipofectamine 3000 (a product of Invitrogen). The introduction was carried out according to the manual attached to the reagent. The plasmid DNA added to the PBMC to make 2.4 μg/well and was cultured at 37° C. in a 5%-$CO_2$ atmosphere.

—Measurement (NanoLuc Luminescence Assay) of NanoLuc Expression (Luminescence Intensity)

48 hours after the addition of the plasmid DNA using the DNA-encapsulating carrier or Lipofectamine 3000, each culture plate is taken out of the incubator, and a luminescence image of the NanoLuc-positive cells was taken with a luminescence microscope system (a product of Olympus). The luminescence intensity of NanoLuc was obtained from the photography of the luminescence image using image processing software (ImageJ).

—Measurement of GFP Expression

Next, 24 hours after the addition of the mRNA using the RNA-encapsulating carrier or lipofectamine 3000, each culture plate was taken out of the incubator, and the cells were collected by centrifuging. Thereafter, the resultant was washed once with a phosphate-buffered saline (PBS), and resuspended in the PBS, and then the green fluorescent of GFP was detected by a fluorescence-activation cell sorter (FACS, FACS Verse (registered trademark), a product of BD bioscience).

—Results

Figure 7:
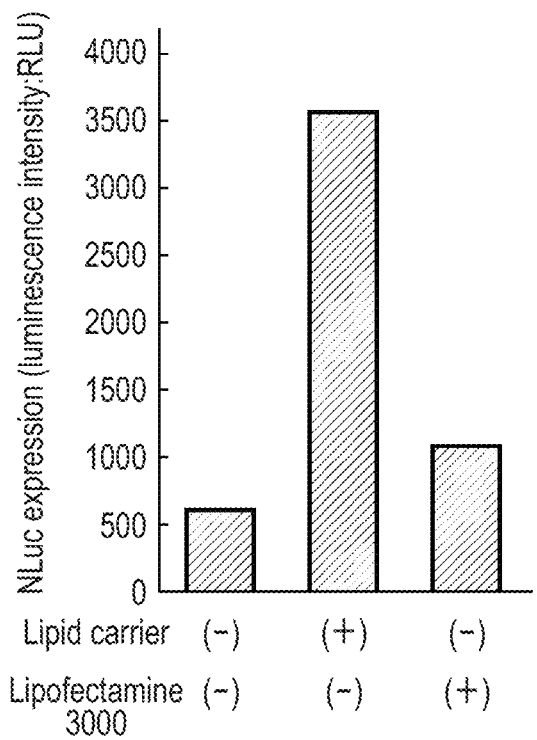
FIG. 7 is a graph illustrating a test result (NanoLuc luminescence intensity) in Example 1.

FIG. 7 shows results of the measurement of the intensity of the NanoLuc luminescence. In the case where the introduction was carried out by using the DNA-encapsulating carrier (that is, the nucleic acid-introducing carrier (+) but the lipofectamine 3000 (−)), an luminescence intensity of as high as approximately 3.5 times of that of the case where the introduction was carried out by using Lipofectamine 3000 (the nucleic acid-introducing carrier (−) and the lipofectamine 3000 (+)). As a result, in the cells in which DNA was introduced using the DNA-encapsulating carrier, it is clear that DNA was well introduced and the NanoLuc gene was well expressed. This fact indicates that the method of introduction by encapsulating DNA in a lipid particle shows higher DNA introduction efficiency and high gene expression efficiency than that of the method using the complex of lipofectamine and DNA.

Figure 8:
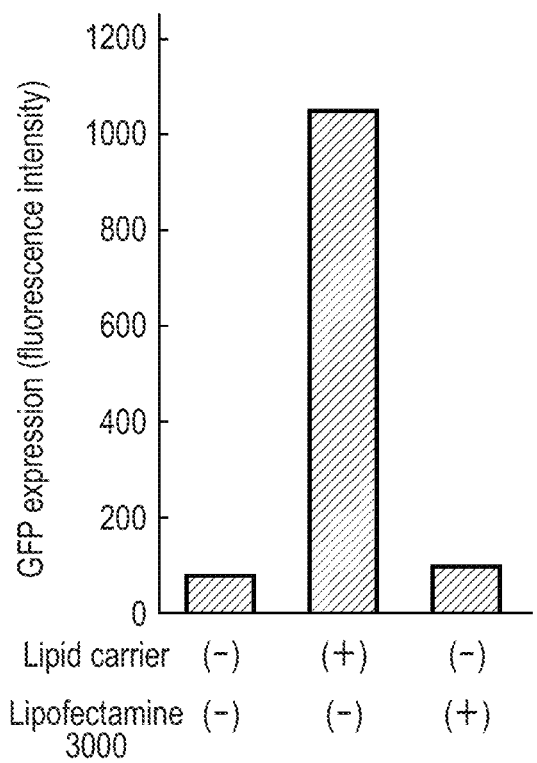
FIG. 8 is a graph illustrating a test result (GFP fluorescence intensity) in Example 1.

FIG. 8 shows results of the measurement of the GFP fluorescence intensity. In the case where the introduction was carried out by using the RNA-encapsulating carrier (that is, the nucleic acid-introducing carrier (+) but the lipofectamine 3000 (−)), a fluorescence intensity of as high as approximately 10 times of that of the case where the introduction was carried out by using the lipofectamine 3000 (the nucleic acid-introducing carrier (−) and the lipofectamine 3000 (+)). As a result, in the cells in which RNA was introduced using the RNA-encapsulating carrier, it is clear that RNA was well introduced and the GFP gene was well expressed. This fact indicates that the method of introduction by encapsulating RNA in a lipid particle shows higher RNA introduction efficiency and high gene expression efficiency than that of the method using the complex of lipofectamine and RNA.

Example 2: Evaluation of Nucleic Acid Introduction Ratio to PBMC Cells by DNA-Encapsulating Lipid Particles Containing Biodegradable Lipid —Preparation of DNA-Encapsulating Carrier As DNA, plasmid DNA in which NanoLuc gene is linked to a downstream of a cytomegalovirus promoter was used. To a DNA solution containing this DNA, cationic peptide was added and thus a DNA-peptide complex was formed. Then, the resultant was added to three kinds of ethanol-dissolved lipid solutions ((1): FFT10/DOTAP/cholesterol/PEG-DMG=74/21/60/4 mol, (2): FFT10/SST04 (lipid compound of Formula (2-01) above)/DOTAP/cholesterol/PEG-DMG=37/7.5/21/60/4 mol, (3): DOTAP/cholesterol/PEG-DMG=21/30/2 mol), respectively, and further 10 mM of HEPES (pH 7.3) was added gently thereto. Thereafter, the resultant was washed and concentrated by centrifuging ultrafiltration, and thus a DNA-encapsulating carrier was obtained. The encapsulated DNA amount of the nucleic acid-introducing carrier was measured with Quant-iT (registered trademark) PicoGreen dsDNA Assay Kit (a product of Thermo Fischer Scientifics), and it was confirmed that a sufficient quantity of DNA was encapsulated.

—Preparation of PBMC

Human peripheral blood mononuclear cells (PBMC) were cultured in TexMACS culture medium (a product of Miltenyi Biotech), and the cells were collected by centrifuging. After that, the cells were suspended in fresh TexMACS to make $2.0 \times 10^6$ cells/mL. 200 μL of the cell suspension was added to a 96-well culture plate to make $4.0 \times 10^6$ cells/well.

—Introduction of Nucleic Acid by DNA-Encapsulating Carrier

Then the DNA-encapsulating carrier was added to the well so as to make 0.5 μg/well of DNA, and it was cultured at 37° C. in a 5%-$CO_2$ atmosphere.

—Measurement of NanoLuc Expression (Luminescence Intensity) (NanoLuc Luminescence Assay)

48 hours after the addition of plasmid DNA by mixing with the DNA-encapsulating carrier, the culturing plate was taken out of the incubator and the luminescence intensity of NanoLuc was measured with a luminometer (Infinite (registered trademark) F200PRO, a product of Tecan) using Nano-Glo Luciferase Assay System (a product of Promega). The measurement was conducted according to the manuals attached to the kit and the device.

—Results

Figure 9:
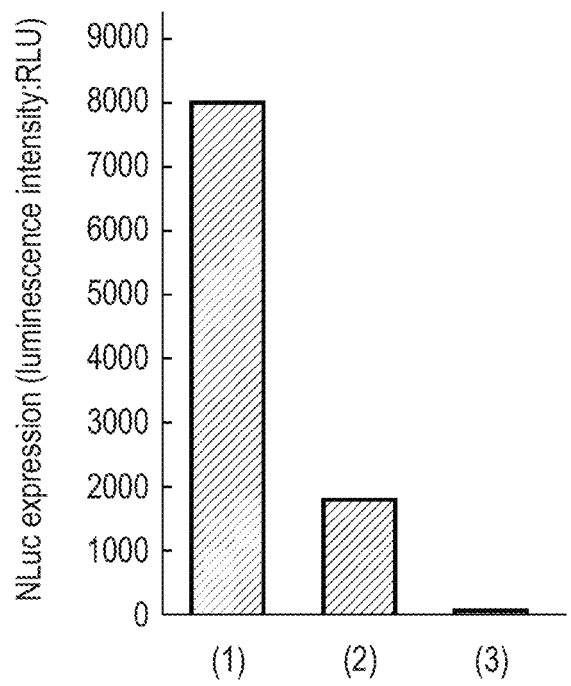
FIG. 9 is a graph illustrating a test result (NanoLuc luminescence intensity) in Example 2.
Figure 10:
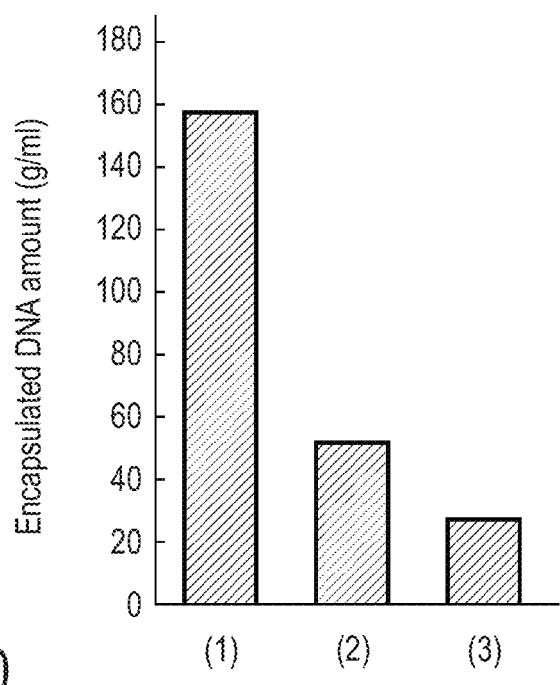
FIG. 10 is a graph illustrating a test result (Encapsulated DNA amount) in Example 2.

FIG. 9 shows results of measurement of the NanoLuc luminescence intensity and FIG. 10 shows results of measurement of the encapsulated DNA amount. In the case where a lipid particle (1) containing a biodegradable lipid was used, approximately 157 times of the luminescence intensity and 5 times or more of the encapsulated DNA amount were obtained as compared to the case where a lipid particle (3) which did not contain a biodegradable lipid was used. In the case where a lipid particle (2) containing a biodegradable lipid was used, approximately 36 times of the luminescence intensity and approximately 2 times of the encapsulated DNA amount were obtained as compared to the case where the lipid particle (3) was used. From the results, it is clear that the encapsulated amount of nucleic acid is improved and also the genetic expression is greatly improved when a lipid particle containing a biodegradable lipid is used. This fact indicates that when a lipid particle containing a biodegradable lipid is used, the efficiency of introduction of nucleic acid is very much raised.

From the comparison between the case of using the lipid particle (1) and the case of using the lipid particle (2), it is clear that the case of using the lipid particle (1) exhibits approximately 4 times and approximately 3 times as high as the NanoLuc luminescence intensity and encapsulated DNA amount, respectively. Thus, it was demonstrated that the efficiency of introduction of nucleic acid is raised more when the lipid (1) is used.

Example 3: Evaluation of Introduction Ratio of Nucleic Acid to PBMC Cells by DNA-Encapsulating Lipid Particle Containing Biodegradability Lipid —Preparation of DNA-Encapsulating Carrier As the DNA, a plasmid DNA in which the NanoLuc gene was linked to a downstream of the cytomegalovirus promoter was used. To a DNA solution containing this DNA, cationic peptide was added, and thus a DNA-peptide complex was formed. Then, the resultant was added to ten kinds of ethanol dissolution lipid solutions shown in Table 4, respectively, and further 10 mM of HEPES (pH 7.3) was gently added thereto. After that, it was washed and concentrated by centrifuging ultrafiltration and thus a DNA-encapsulating carrier was obtained.

TABLE 4

| Composition | FFT10 | DOPE | DOTAP | Cholesterol | PEG-DMG |
|---|---|---|---|---|---|
| 4 | 37 | 5.25 | 10.5 | 15 | 1 |
| 5 | 37 | 5.25 | 5.25 | 30 | 2 |
| 6 | 37 | 5.25 | 10.5 | 60 | 4 |
| 7 | 18.5 | 0 | 10.5 | 30 | 2 |
| 8 | 74 | 5.25 | 10.5 | 30 | 2 |
| 9 | 37 | 5.25 | 10.5 | 30 | 2 |
| 10 | 37 | 10.5 | 10.5 | 30 | 2 |
| 11 | 18.5 | 0 | 21 | 60 | 4 |
| 12 | 37 | 0 | 42 | 30 | 2 |
| 13 | 18.5 | 0 | 42 | 30 | 2 |

(Unit: Molar ratio)

The encapsulated DNA amount of the nucleic acid-introducing carrier was measured with Quant-iT (registered trademark) PicoGreen dsDNA Assay Kit (a product of Thermo Fischer scientific), and was confirmed that a sufficient quantity of DNA was contained.

—Preparation of PBMC

Human peripheral blood mononuclear cells (PBMC) were cultured in TexMACS culture medium (a product of Miltenyi Biotech), and the cells were collected by centrifuging. After that, the cells were suspended in fresh TexMACS to make $2.0 \times 10^6$ cells/mL. 200 μL of the cell suspension was added to a 96-well culture plate to make $4.0 \times 10^6$ cells/well.

—Introduction of Nucleic Acid by DNA-Encapsulating Carrier

Then, the DNA-encapsulating carrier was added to the well so as to make 0.5 μg/well of DNA, and it was cultured at 37° C. in a 5%-$CO_2$ atmosphere.

—Measurement of Acid Dissociation Constant of Nucleic Acid-Introducing Carrier

With an automatic titration device, Zetasizer Nano, (a product of Malvern), the acid dissociation constant pka (pH at which zeta-potential becomes 0) of the nucleic acid-introducing carrier was measured. The pH was adjusted using hydrochloric acid and sodium hydroxide.

—Measurement of NanoLuc Expression (NanoLuc Luminescence Assay)

48 hours after the addition of the plasmid DNA by mixing with the DNA-encapsulating carrier, the culturing plate was taken out of the incubator and the luminescence intensity of NanoLuc was measured with a luminometer (Infinite (registered trademark) F200PRO, a product of Tecan) using Nano-Glo Luciferase Assay System (a product of Promega). The measurement was conducted according to the manuals attached to the kit and the device.

—Results

Table 5 shows the acid dissociation constant (pKa) of the lipid particle and the NanoLuc expression (luminescence intensity: RLU).

TABLE 5

| Composition | Acid dissociation constant (pKa) | NanoLuc expression (luminescence intensity: RLU) |
| --- | --- | --- |
| 4 | 6.0 | 4369 |
| 5 | 6.5 | 8239 |
| 6 | 7.5 | 13277 |
| 7 | 7.6 | 8674 |
| 8 | 8.0 | 1500 |
| 9 | 8.1 | 1493 |
| 10 | 8.4 | 1038 |
| 11 | 9.0 | 1730 |
| 12 | 9.5 | 189 |
| 13 | 9.8 | 101 |

Figure 11:
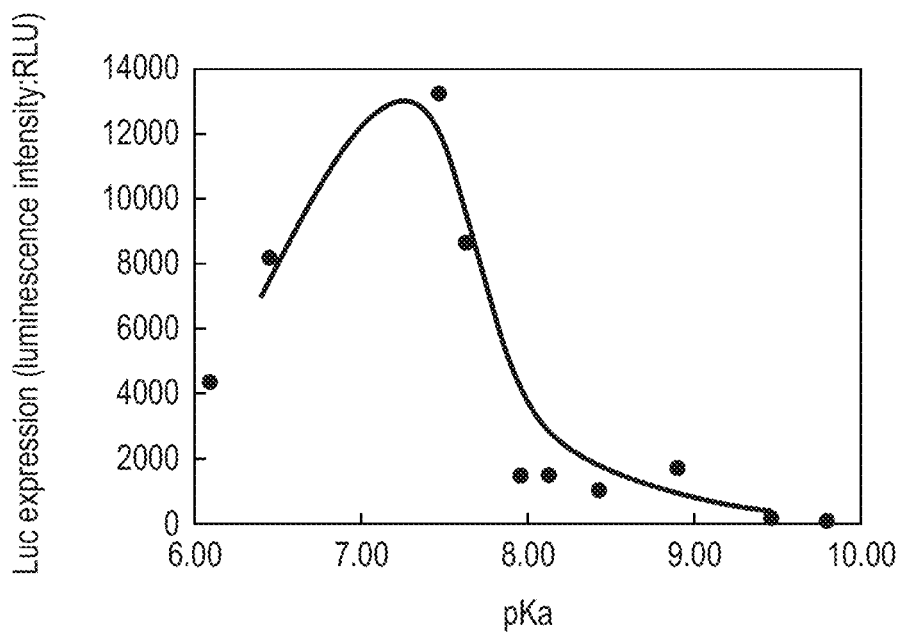
FIG. 11 is a graph illustrating a relationship between the NanoLuc luminescence intensity and pKa in a nucleic acid-introducing carrier produced in Example 3.

Further, FIG. 11 shows the relationship between the NanoLuc expression and the acid dissociation constant of the lipid particle. As is clear from the results shown in Table 5 and FIG. 11, between pKas of 6.5 and 7.6, a NanoLuc expression high as 8000RLU or higher was obtained. Thus, it was demonstrated that the lipid particles of the compositions of 5, 6 and 7 are particularly superior in the nucleic acid introduction efficiency.

Example 4: Evaluation of Introduction Ratio of Nucleic Acid to PBMC Cells by DNA and mRNA-Encapsulating Lipid Particle Containing Biodegradability Lipid —Preparation of DNA-Encapsulating Carrier As the DNA, a plasmid DNA in which the NanoLuc gene was linked to a downstream of the cytomegalovirus promoter and a plasmid DNA in which the GFP gene was linked to a downstream of the cytomegalovirus promoter were used. To DNA solutions respectively containing these DNAs, cationic peptide was added, and thus DNA-peptide complexes were formed. Then, they were added to ethanol-dissolved lipid solutions ((6) FFT10/DOTAP/DOPE/cholesterol/PEG-DMG=37/10.5/5.25/60/4 mol). After that, 10 mM of HEPES (pH 7.3) was added gently to each, and the solutions were washed and concentrated by centrifuging ultrafiltration, thus obtaining a NanoLuc-DNA-encapsulating carrier and GFP-DNA-encapsulating carrier. The encapsulated DNA amounts of the nucleic acid-introducing carriers were measured with Quant-iT (registered trademark) PicoGreen dsDNA Assay Kit (a product of Thermo Fischer Scientifics), and it was confirmed that a sufficient quantity of DNA was encapsulated in each case.

—Preparation of RNA-Encapsulating Carrier

As messenger-RNA (mRNA), mRNA of a green fluorescent protein (GFP), which is a reporter gene (a product of OZ Biosciences), was used. An RNA solution containing this mRNA was added to an ethanol-dissolved lipid solution ((6) FFT10/DOTAP/DOPE/cholesterol/PEG-DMG=37/10.5/5.25/60/4 mol), and suspended with pipetting. After that, 10 mM of HEPES (pH 7.3) was added gently, and the solution was washed and concentrated by centrifuging ultrafiltration, thus obtaining a GFP-RNA-encapsulating carrier. The amount of RNA which encapsulated in the nucleic acid-introducing carrier was measured with QuantiFluor (registered trademark) of RNA System (a product of Promega), and it was confirmed that a sufficient quantity of mRNA was encapsulated.

—Preparation of PBMC

Human peripheral blood mononuclear cells (PBMC) were cultured in a TexMACS culture medium (a product of Miltenyi Biotech), and the cells were collected by centrifuging. After that, the cells were suspended in fresh TexMACS to make $3.3 \times 10^6$ cells/mL. 300 μL of the cell suspension was added to a 4-well culture dish (Matsunami) to make $1.0 \times 10^6$ cells/well.

—Introduction of Nucleic Acid by DNA-Encapsulating Carrier and RNA-Encapsulating Carrier Then, the NanoLuc-DNA-encapsulating carrier and the GFP-DNA-encapsulating carrier were added to the above-described same well to make 2.4 μg/well for each, a total of 4.8 μg/well (DNA×DNA co-introduction). Further, the NanoLuc-DNA-encapsulating carrier and the GFP-RNA-encapsulating carrier were added to the above-described same well to make 2.4 μg/well for each of DNA and RNA, a total of 4.8 μg/well (DNA×RNA co-introduction). Then, after addition of lipid particles, the cells were cultured at 37° C. in a 5%-$CO_2$ atmosphere.

—Measurement of NanoLuc Expression and the GFP Expression 24 hours after the addition of the nucleic acid-introducing carrier, each culture plate was taken out of the incubator, and the luminescence intensity of NanoLuc and the fluorescence intensity of GFP were measured with a light-emitting microscope system and a fluorescence-activation cell sorter (FACS) described in Example 1, respectively.

—Results

Figure 12:
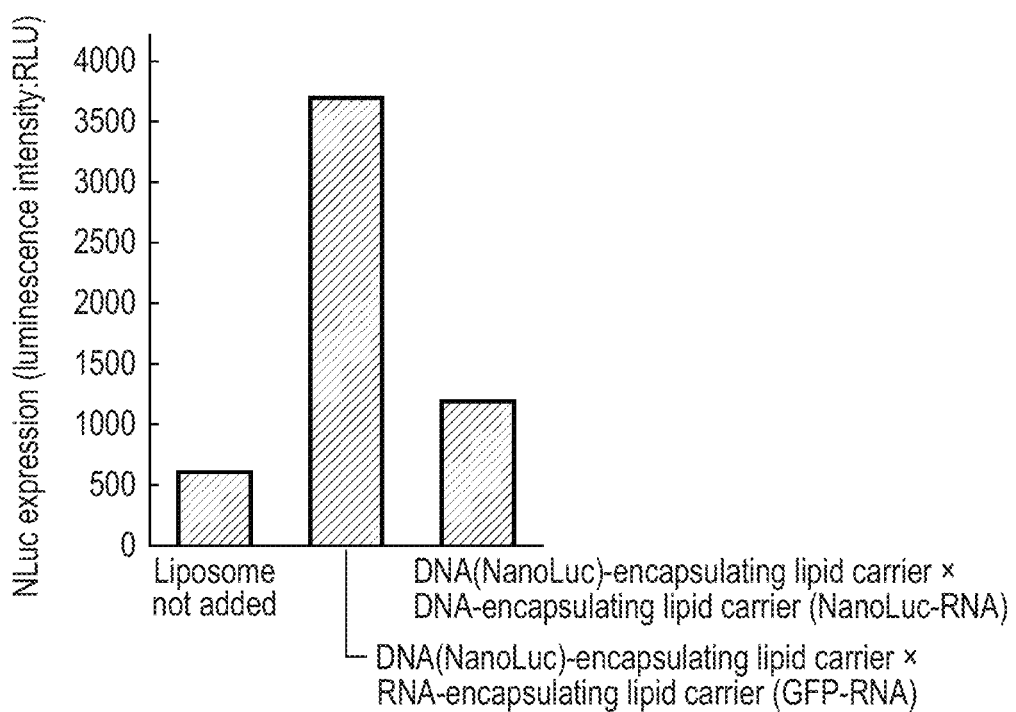
FIG. 12 is a graph illustrating a test result (NanoLuc luminescence intensity) in Example 4.

FIG. 12 shows results of the measurement of the NanoLuc luminescence intensity and FIG. 13 shows results of measurement of the GFP fluorescence intensity. In the case of co-introducing the GFP gene in the RNA form (DNA×RNA CO-introduction), approximately 3 times of the luminescence intensity of NanoLuc was obtained as compared to the case of introducing the gene in the form of DNA (DNA×DNA CO-introduction). Further, for the GFP fluorescence intensity as well, in the case of DNA×RNA co-introduction, 2 times or more of the intensity was obtained as compared to the case of the DNA×DNA co-introduction. From these results, it is clear that the expression amounts of DNA and RNA were higher in the case of co-introduction in the forms of two different types of nucleic acids (DNA and RNA) than in the case where both genes are co-introduced in the form of DNA.

Example 5: Evaluation of CAR Gene Introduction Efficiency by Simultaneous Introduction of CAR-DNA-Encapsulating Carrier and piggyBac mRNA-Encapsulating Carrier —Preparation of CAR-DNA-Encapsulating Carrier As the DNA, a plasmid DNA in which a CAR gene expression cassette linking CAR gene and a cytomegalovirus promoter was inserted between piggyBac recognition sequences (5' ITR and 3' ITR), was used. Then, a DNA solution including the CAR-DNA was added to an ethanol dissolution lipid solution ((14) FFT10/DOTAP/cholesterol/PEG-DMG=37/21/30/2 mol), and suspended with pipetting. After that, 10 mM of HEPES (pH 7.3) was gently added, and this solution was washed and concentrated by centrifuging ultrafiltration. Thus, the CAR-DNA-encapsulating carrier was obtained.

—Preparation of piggyBac mRNA-Encapsulating Carrier

For piggyBac mRNA, RNA was synthesized from an in-vitro transcription plasmid DNA in which the piggyBac gene was linked with the T7 promoter using a commercially available in-vitro transcription RNA synthesizing kit (CUGA7 in-vitro transcription kit, a product of NIPPON GENE). With a commercially available kit, a Cap structure was added to the 5' end of the RNA and a poly A structure was added to the 3' end, and thus a piggyBac mRNA was obtained. The synthesis of the mRNA was conducted according to the manual attached to the kit. An RNA solution containing the piggyBac mRNA was added to an ethanol dissolution lipid solution ((15) FFT10/DOPE/cholesterol/PEG-DMG=37/21/30/2 mol), and suspended with pipetting. After that, 10 mM of HEPES (pH 7.3) was gently added, and this solution was washed and concentrated by centrifuging ultrafiltration. Thus, the piggyBac-RNA-encapsulating carrier was obtained.

—Preparation of CAR-DNA/piggyBac-DNA-Encapsulating Carrier

As a control for comparison, a mixture solution of CAR-DNA and a plasmid DNA in which the piggyBac is linked with the cytomegalovirus promoter was added to an ethanol dissolution lipid solution ((14) FFT10/DOTAP/cholesterol/PEG-DMG=37/21/30/2 mol), and further 10 mM of HEPES (pH 7.3) was gently added. After that, the resultant was washed and concentrated by centrifuging ultrafiltration, and thus the CAR-DNA/piggyBac-DNA-encapsulating carrier was obtained.

—Preparation of Cells and Introduction of Nucleic Acid by Nucleic Acid-Introducing Carrier Frozen commercially available human peripheral blood mononuclear cells (PBMC, Lonza) were thawed at 37° C. in a thermostatic bath, and then the cells were collected by centrifuging. The cells were suspended in TexMACS containing two kinds of cytokines (10 ng/ml of IL-7 and 5 ng/ml of IL-15 (Miltenyi)), and then seeded on a 6-cm culturing dish, followed by culturing in the incubator at 37° C. in a 5%-$CO_2$ atmosphere. After culturing one night, the culture dish was taken out of the incubator, and the cells were collected by centrifuging. Then, the cells were suspended in TexMACS (containing 10 ng/ML of IL-7 and 5 ng/ml of IL-15) and cultured on a 48-well culture plate coated with anti-CD3 antibody (Miltenyi) and CD28 antibody (Miltenyi) at 37° C. in a 5%-$CO_2$ atmosphere one night.

To the cell culture solution, CAR-DNA-encapsulating carrier (4 µg) and piggyBac-RNA-encapsulating carrier (4 µg) were added and the solution was gently mixed with pipetting. Then, the culture was continued at 37° C. in a 5%-$CO_2$ atmosphere. Further, as a control for comparison, a CAR-DNA/piggyBac-DNA-encapsulating carrier (4 µg, 4 µg respectively) was added to a cell culture liquid and the liquid was gently mixed with pipetting. Then, the culture was continued at 37° C. in a 5%-$CO_2$ atmosphere.

—Detection of CAR-Expression T Lymphocytes Cells 7 days after the addition of the nucleic acid-introducing carriers, the culture plate was taken out of the incubator, and the cells were collected by centrifuging. The cells were suspended in a phosphate-buffered saline (PBS) and then an anti-human IgG antibody (Fluorescein (FITC) F(ab')$_2$ Fragment Goat Anti-Human IgG (H+L) of Jackson ImmunoResearch Inc.) and an anti-CD3 antibody (V450 mouse anti-human CD3, clonal UCHT1, a product of BD bioscience), was added to react with cells. After the reaction was finished, the cells were collected by centrifuging and washed with a PBS containing 1% of bovine serum albumin. Then, the cells were re-suspended in a PBS containing 1%-BSA, and thus a test sample of FACS was prepared. In the FACS, anti-IgG antibody-binding cells (CAR expression cells) and anti-CD3 antibody-binding cells (T lymphocytes cells) were detected by an APC filter set and a V450 filter set, respectively.

—Results

Figure 14:
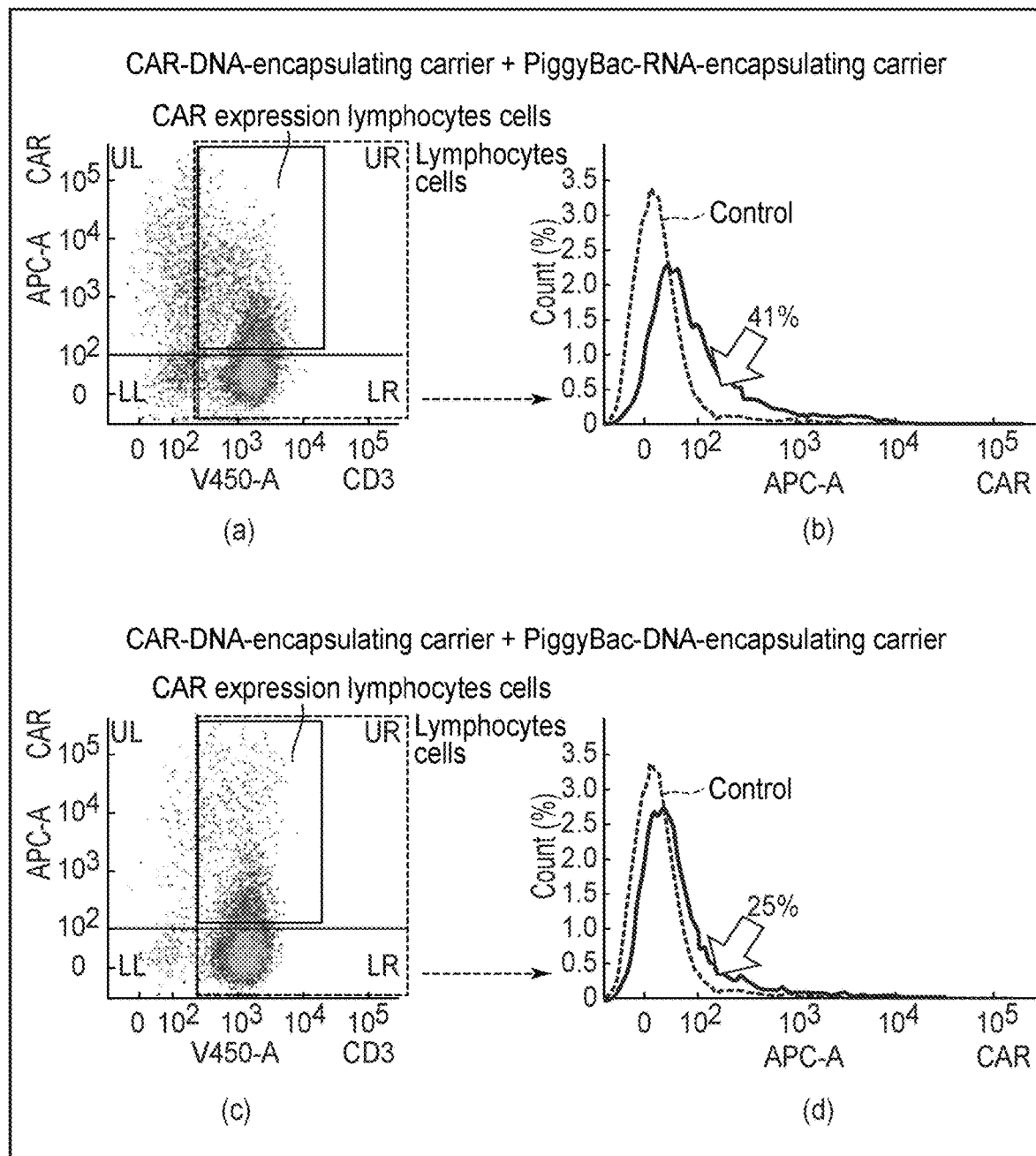
FIG. 14 is a histogram showing a test result of FACS in Example 5.

FIG. 14 show the results. FIG. 14, parts (a) and (b) show the results when the CAR-DNA-encapsulating carrier and the piggyBac-RNA-encapsulating carrier were introduced. FIG. 14, parts (c) and (d) show the results when the CAR-DNA/piggyBac-DNA-encapsulating carrier was introduced.

FIG. 14, parts (a) and (c) show 2-color dot plots in which CD3 and IgG were indicated by vertical and lateral axes, respectively. From the dot plots, it is clear that $CD3^+$ cells (T lymphocytes cells) and $IgG^+$ cells (CAR expression cells) are present in a UR fraction. The results indicate that the DNA was introduced to the cells and the CAR gene was expressed.

FIG. 14, parts (b) and (d), show histograms in which the number of cells (%) and the intensity of fluorescence from a fluorescence-labeled antibody are indicated by vertical and lateral axes, respectively. The broken line indicates results for cells in which DNA and RNA were not introduced (the control), whereas the solid line indicates results for the cells in which the nucleic acid-introducing carrier was added. In the histogram of FIG. 14, part (b) or (d), the ratio of the region defined by the solid line, which do not overlap the region defined by the broken line (the region indicated by an arrow in the figure) indicates the ratio of the CAR-T cells, that is, the $CD3^+$ and $CAR^+$ cells. When the CAR-DNA-encapsulating carrier and the piggyBac-RNA-encapsulating carrier were used, the ratio was 41%. On the other hand, when the CAR-DNA-encapsulating carrier and the piggyBac-DNA-encapsulating carrier were used, it was 25%. Thus, it is clear that the efficiency of production of the CAR-T cells is higher when the piggyBac was introduced into cells in the form of RNA than when introduced in the form of DNA.

Example 6: Preparation of CAR-T Cells Using CAR-DNA and piggyBac-mRNA-Encapsulating Lipid Particles which Contain Biodegradable Lipids —Preparation of CAR-DNA-Encapsulating Carrier As the DNA, a plasmid DNA in which the CAR gene (CD19. CAR gene) was linked to a downstream of the cytomegalovirus promoter, was used. To a DNA solution containing the DNA, cationic peptide was added, and thus a DNA-peptide complex was formed. Then, the resultant was added to an ethanol dissolution lipid solution ((16): FFT10/DOTAP/DOPE/cholesterol/PEG-DMG=37/5.25/10.5/60/4 mol, (17): FFT20 (lipid compound of formula (1-02) provided above)/DOTAP/DOPE/cholesterol/PEG-DMG=37/10.5/5.25/60/4 mol), and further 10 mM of HEPES (pH 7.3) was gently added. After that, the resultant was washed and concentrated by centrifuging ultrafiltration, and thus the DNA-encapsulating carrier was obtained.

—Preparation of RNA-Encapsulating Carrier

As the messenger RNA (mRNA), mRNA of the piggyBac gene was used. An RNA solution containing the mRNA was added to two kinds of ethanol dissolution lipid solutions ((16): FFT10/DOTAP/DOPE/cholesterol/PEG-DMG=37/5.25/10.5/60/4 mol, (17): FFT20/DOTAP/DOPE/cholesterol/PEG-DMG=37/10.5/5.25/60/4 mol) and suspended with pipetting. After that, 10 mM of HEPES (pH 7.3) was gently added, and the solutions were washed and concentrated by centrifuging ultrafiltration. Thus, the RNA-encapsulating carrier was obtained.

—Preparation of PBMC

Human peripheral blood mononuclear cells (PBMC) were cultured in a TexMACS culture medium (a product of Miltenyi Biotech), and the cells were collected by centrifuging. After that, the cells were suspended in fresh TexMACS to make $2.0 \times 10^6$ cells/mL. 500 μL of the cell suspension was added to a 48-well culture plate to make $1.0 \times 10^6$ cells/well.

—Introduction of Nucleic Acid by DNA-Encapsulating Carrier and RNA-Encapsulating Carrier Then, the DNA-encapsulating carrier and the RNA-encapsulating carrier were added to the well to make 4.0 μg/well for each of DNA and RNA, a total of 8.0 μg/well and were cultured at 37° C. in a 5%-$CO_2$ atmosphere.

—Measurement of CAR Expression 7 days and 14 days after the addition of the nucleic acid-introducing carriers, each culture plate was taken out of the incubator, and the cells were collected by centrifuging. The cells were suspended in a phosphate-buffered saline (PBS) and then an anti-human IgG antibody (Fluorescein (FITC) F(ab')$_2$ Fragment Goat Anti-Human IgG (H+L) of Jackson ImmunoResearch Inc.) and an anti-CD3 antibody (V450 mouse anti-human CD3, clonal UCHT1, a product of BD bioscience) was added to react with cells. After the reaction was finished, the cells were collected by centrifuging and washed with a PBS. Then, the cells were re-suspended in a PBS, and thus a test sample of FACS was prepared. In the FACS, anti-IgG antibody-binding cells (CAR expression cells) and anti-CD3 antibody-binding cells (T lymphocytes cells) were detected by an APC filter set and a V450 filter set, respectively.

—Results

Figure 15:
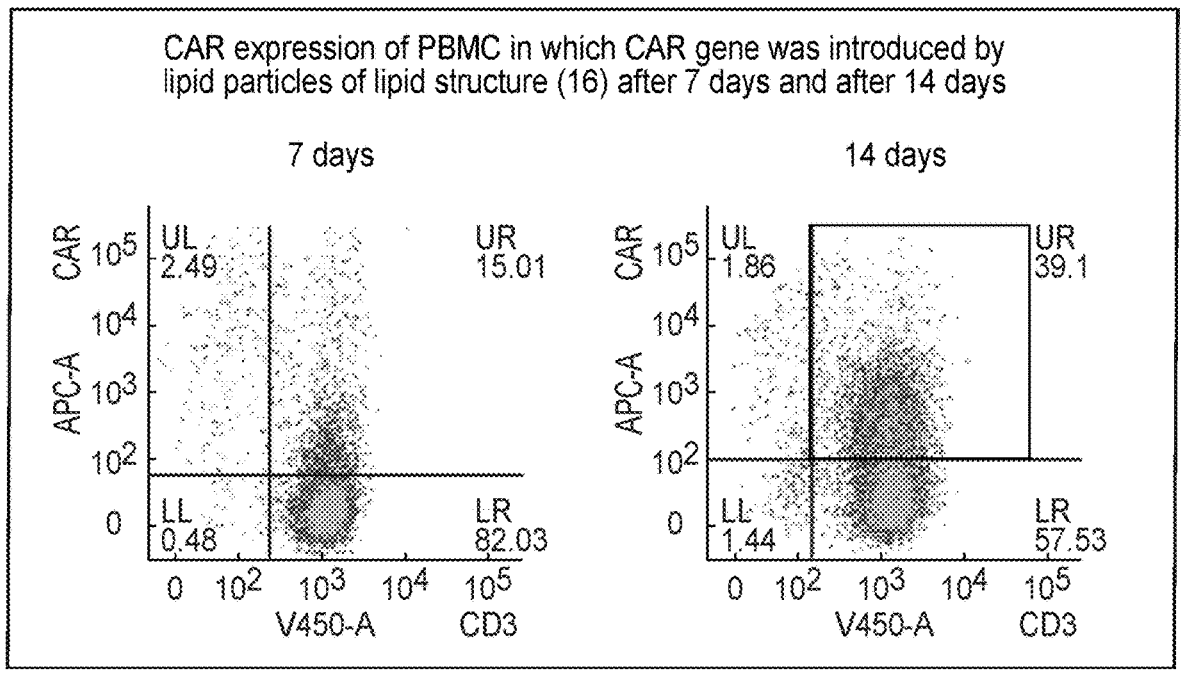
FIG. 15 is a histogram showing a test result of FACS in Example 6.
Figure 16:
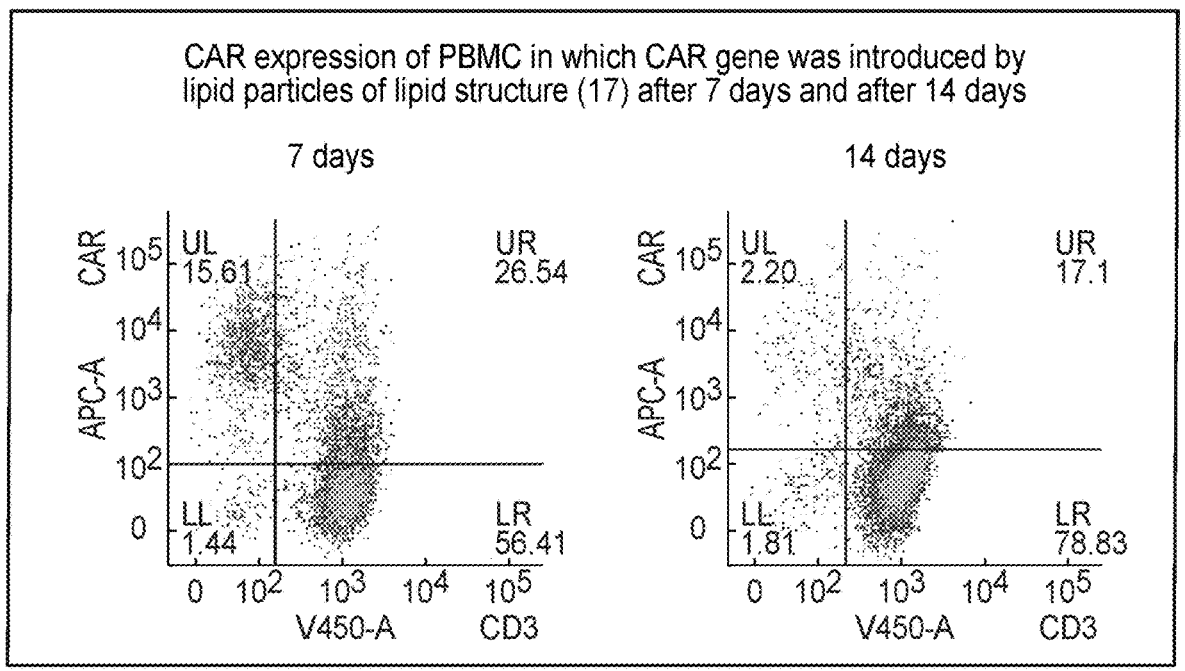
FIG. 16 is a histogram showing a test result of FACS in Example 6.

FIGS. 15 and 16 shows results of the measurements. FIG. 15 shows the result in the case of using the lipid particles of the lipid composition (16) after 7 days later and after 14 days of culture. FIG. 15 shows dot plots in which the CD3 expression (CD3$^+$) and CAR expression (IgG$^+$) of PBMC are indicated by the vertical and horizontal axes, respectively. FIG. 16 shows dot plots in the culturing after 7 days and after 14 days in the case where the nucleic acid-introducing carrier of the lipid composition (17) was used.

From the dot plots, it is clear that CD3$^+$ cells (T lymphocytes cells) and IgG$^+$ cells (CAR expression cells), that is, CAR-T cells, are present in a UR fraction. When the lipid particles (16) were used, the ratio of CAR-T cells on the seventh day was 15.0%, and the ratio of CAR-T cells on the fourteenth day was 39.1%. When the lipid particles (17) were used, the ratio of CAR-T cells on the seventh day was 26.5%, and the ratio of CAR-T cells on the fourteenth day was 17.1%.

From these results, it is clear that the CAR-T cells can be prepared by a lipid particle containing biodegradable lipid as its main component.

Example 7: Evaluation of Antitumor Effect of CAR-T Cells Prepared Using CAR-DNA and piggyBac-mRNA-Encapsulating Lipid Particle Containing Biodegradable Lipid —Preparation CAR-DNA-Encapsulating Carrier As the DNA, a plasmid DNA in which the CAR gene (CD19. CAR gene) was linked to a downstream of the cytomegalovirus promoter, was used. To a DNA solution containing the DNA, cationic peptide was added, and thus a DNA-peptide complex was formed. Then, the resultant was added to an ethanol dissolution lipid solution ((14) FFT10/DOTAP/cholesterol/PEG-DMG=37/21/30/2 mol), and further 10 mM of HEPES (pH 7.3) was gently added. After that, the resultant was washed and concentrated by centrifuging ultrafiltration, and thus the DNA-encapsulating carrier was obtained.

—Preparation of RNA-Encapsulating Carrier

As the messenger RNA (mRNA), mRNA of the piggyBac gene was used. An RNA solution containing the mRNA was added to an ethanol dissolution lipid solution ((15) FFT10/DOPE/cholesterol/PEG-DMG=37/21/30/2 mol) and suspended with pipetting. After that, 10 mM of HEPES (pH 7.3) was gently added, and the solutions were washed and concentrated by centrifuging ultrafiltration. Thus, the RNA-encapsulating carrier was obtained.

—Preparation of PBMC

Human peripheral blood mononuclear cells (PBMC) were cultured in a TexMACS culture medium (a product of Miltenyi Biotech), and the cells were collected by centrifuging. After that, the cells were suspended in fresh TexMACS to make $2.0 \times 10^6$ cells/mL. 500 μL of the cell suspension was added to a 48-well culture plate to make $1.0 \times 10^6$ cells/well.

—Introduction of Nucleic Acid by DNA-Encapsulating Carrier and RNA-Encapsulating Carrier Then, the DNA-encapsulating carrier and the RNA-encapsulating carrier were added to the well to make 4.0 μg/well for each of DNA and RNA, a total of 8.0 μg/well and were cultured at 37° C. in a 5%-$CO_2$ atmosphere.

Figure 17:
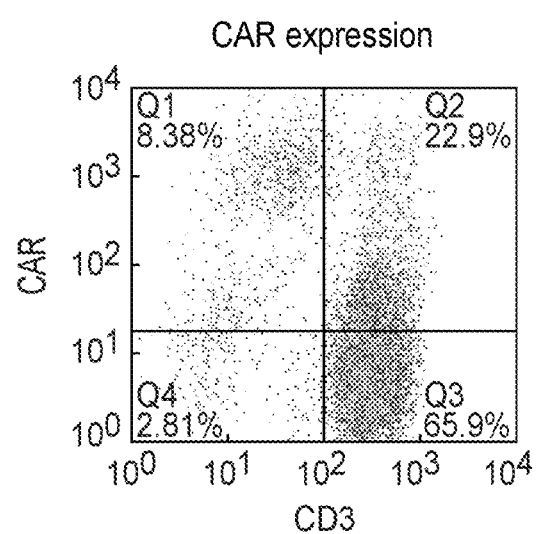
FIG. 17 is a histogram showing a test result of FACS of Example 7.

—Measurement of CAR Expression 14 days after the addition of the nucleic acid-introducing carrier, the culture plate was taken out of the incubator, and the cells were collected by centrifuging. The cells were suspended in a phosphate-buffered saline (PBS) and then an anti-human IgG antibody (Fluorescein (FITC) AffiniPure F(ab')$_2$ Fragment Goat Anti-Human IgG (H+L) of Jackson ImmunoResearch Inc.) and an anti-CD3 antibody (CD3-APC human monoclonal, Miltenyi Biotec) was added to react with cells. After the reaction was finished, the cells were collected by centrifuging and washed with a PBS. Then, the cells were re-suspended in a PBS, and thus a test sample of FACS was prepared. In the FACS, anti-IgG antibody-binding cells (CAR expression cells) and anti-CD3 antibody-binding cells (T lymphocytes cells) were detected by an FITC filter set and an APC filter set, respectively.
—Results FIG. 17 shows results of the CAR expression. From the results, it is clear that the UR fraction contains CD3$^+$ cells (T lymphocytes cells) and IgG$^+$ cells (CAR expression cells), that is, the CAR-T cells, at a ratio of 22.9%.
—Co-Culturing with SUSR Cells As target cells, SU/SR cells of CD19$^+$ tumor cell strain were used. As effector cells, CAR-T cells (CD19.CAR-T cell) cultured for 14 days were used, and T cells without lipid particles being added was used as a control.

Figure 18:
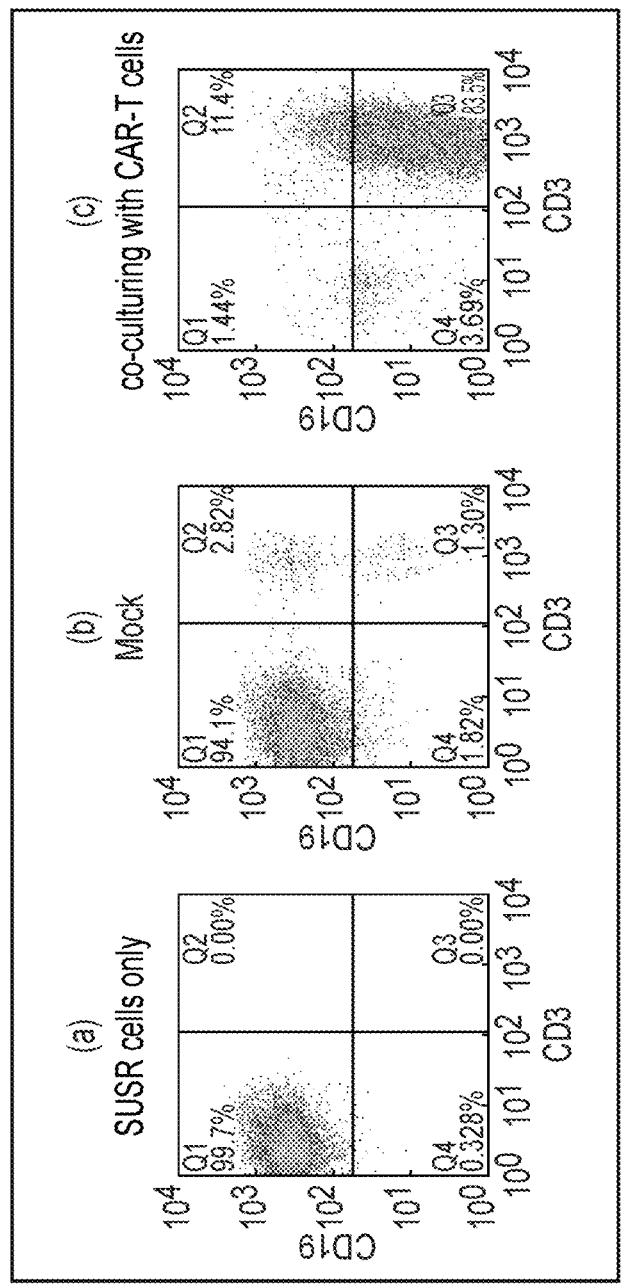
FIG. 18 is a histogram showing a test result of FACS of Example 7.

The effector cells: the target cells were mixed at 1:10, and co-cultured as follows. That is, at a ratio of $5.0 \times 10^5$ cells/well of the target cells and $5.0 \times 10^4$ cells/well of the effector cells, they were subjected to culture on a 48-well culture plate using 1 mL of RPMI-1640 culture medium to which 10%-FBS was added. After 5 days of co-culturing, the culture plate was taken out of the incubator, and the cells were collected by centrifuging. The cells were suspended in a phosphate-buffered saline (PBS) and then an anti-CD19 antibody (CD19-PE human monoclonal, Miltenyi Biotec) and a CD3 antibody (CD3-APC human monoclonal, Miltenyi Biotec) was added to react with cells. After the reaction was finished, the cells were collected by centrifuging and washed with a PBS. Then, the cells were re-suspended in a PBS, and thus a test sample of FACS was prepared. In the FACS, the anti-CD19 antibody-binding cells (SUSR cells, target cells) and the anti-CD3 antibody-binding cells (CAR-T cells, effector cells) were detected by a PE filter set and an APC filter set, respectively. The anti-tumor activity of the CAR-T cells was calculated as the survival rate of SUSR cells, from the data of the FACS.
—Results FIG. 18 shows the results. In the case (a) of SUSR cells only, the anti-CD19 antibody-binding cells (SUSR cells) were detected at a ratio of 99.7%, whereas in the case (c) of co-culturing with CAR-T cells, the anti-CD19 antibody-binding cells (SUSR cells) were detected only 1.44%. This fact indicates that the survival rate of SUSR cells decreased as much as by 98.5% by the presence of the CAR-T cells. Therefore, it has been cleared that the CAR-T cells of the embodiment have excellent anti-tumor activity.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method of producing a genetically modified T cell or CAR-T cell which expresses a chimeric antigen receptor or CAR, comprising:

contacting a T cell by contacting it with a stimulatory antibody comprising at least one of an anti-CD3 antibody and/or an anti-CD28 antibody thereby producing an activated T cell, introducing a first and second nucleic acid into the activated T cell by contacting it with a nucleic acid-introducing carrier thereby producing a genetically modified T cell or CAR-T cell, and culturing the genetically modified T cell or CAR-T cell, wherein the nucleic acid-introducing carrier comprises a lipid particle, wherein the lipid particle comprises a hollow body and encapsulates the first nucleic acid and the second nucleic acid in a lumen of the hollow body, wherein the first nucleic acid comprises a CAR nucleic acid sequence, wherein the second nucleic acid comprises a transposase gene sequence which is encapsulated in the lipid particle, and wherein the lipid particle comprises a first lipid compound and/or a second lipid compound as its component, and the first lipid compound is expressed by Formula:

Q-CHR$_2$ wherein

Q represents a nitrogen-containing aliphatic group containing two or more tertiary nitrogen elements without containing oxygen, R is independently an aliphatic group of $C_{12}$ to $C_{24}$, at least one R contains a linking group LR selected from the group consisting of —C(=O)—O—, —OC(=O)—, —OC(=O)—O—, —S—C(=O)—, —C(=O)—S—, —C(=O)—NH and —NHC(=O)— in a main chain or side chain thereof and wherein the second lipid compound is expressed by Formula:

P—[X—W—Y—W'—Z]$_2$ (where P is represented by alkyleneoxy containing one or more ether bond in a main chain thereof, X is independently a divalent linking group containing a tertiary amine structure, W is independently $C_1$ to $C_6$ alkylene, Y is independently a divalent linking group selected from the group consisting of a single bond, ether bond, carboxylic ester bond, thiocarboxylic ester bond, thioester bond, amide bond, carbamate bond and the urea bond, W' is independently a single bond or alkylene, and Z is independently a fat soluble vitamin residue, sterol residue or $C_{12}$ to $C_{22}$ aliphatic hydrocarbon group.

2. The method of claim 1, wherein the first lipid compound is expressed by Formula:

Q-CHR$_2$ wherein

Q represents a nitrogen-containing aliphatic group containing two or more tertiary nitrogen elements without containing oxygen, R is independently an aliphatic group of $C_{12}$ to $C_{24}$, and contains R1-C(=O)—O—R2 wherein R1 is alkylene and R2 is alkenyl.

3. The method of claim 1, wherein the lipid particle further comprises at least one of a lipid which adjusts surface charge of the nucleic acid-introducing carrier and a lipid which suppresses aggregation between the nucleic acid-introducing carriers.

4. The method of claim 1, wherein the lipid particle has an acid dissociation constant of 6.5 to 8.0.

5. The method of claim 4, wherein the lipid particle has an acid dissociation constant of 7.5 to 8.0.

6. The method of claim 1, wherein the first nucleic acid and the second nucleic acid are DNA, RNA, PNA or a derivative of any of these.

7. The method of claim 6, wherein the first nucleic acid comprises DNA and the second nucleic acid comprises RNA.

8. The method of claim 1, wherein the first nucleic acid and the second nucleic acid each are a single- or double-stranded, annular, linear-chain or branched-chain nucleic acid.

9. The method of claim 1, wherein the first nucleic acid and the second nucleic acid are, respectively, RNA and DNA, or DNA and RNA or are different structurally-distinct nucleic acids.

10. The method of claim 1, wherein the first nucleic acid and the second nucleic acid are encapsulated together in the lipid particle, or in separate ones of the lipid particle.

11. The method of claim 1, wherein the transposase is piggyBac.

12. The carrier of claim 2, wherein
the lipid particle comprises the first lipid compound and further comprises cationic lipids,
the first lipid compound comprises 20% in molar ratio of the entire lipid particle, and
a ratio of molar concentration of the cationic lipids to molar concentration of the first lipid compound is 0.5 or more.

13. The method of claim 2, wherein the first lipid compound is at least one selected from the group of following chemical formulas,

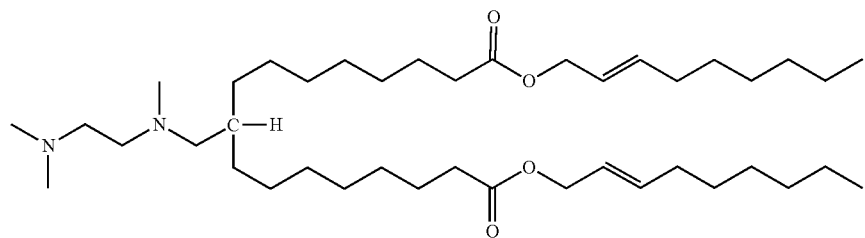
(1-01)
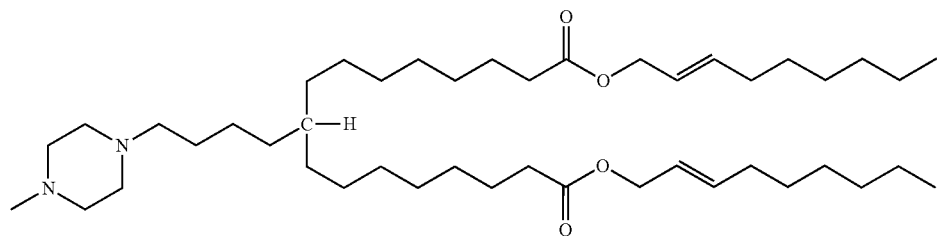
(1-02)
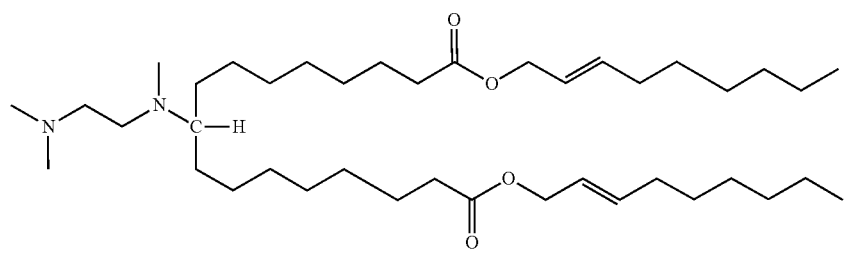
(1-03)
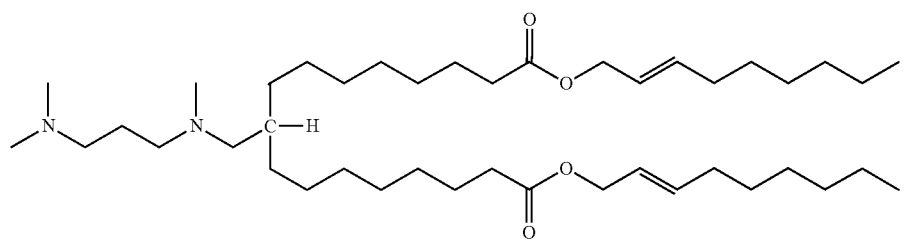
(1-04)
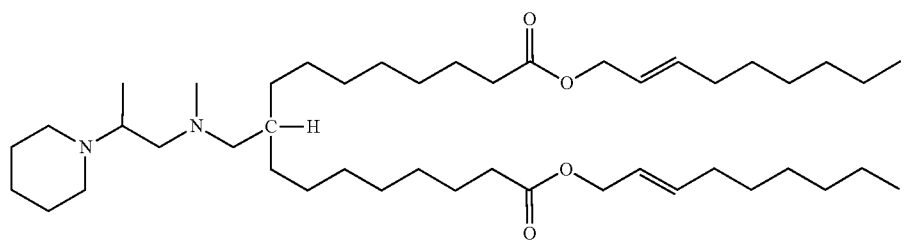
(1-05)
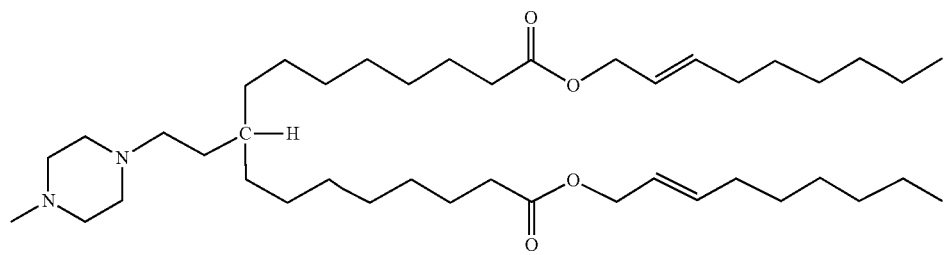
(1-06)

(1-07)
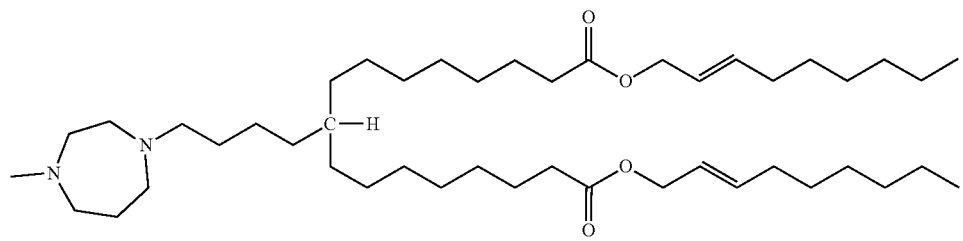
(1-08)
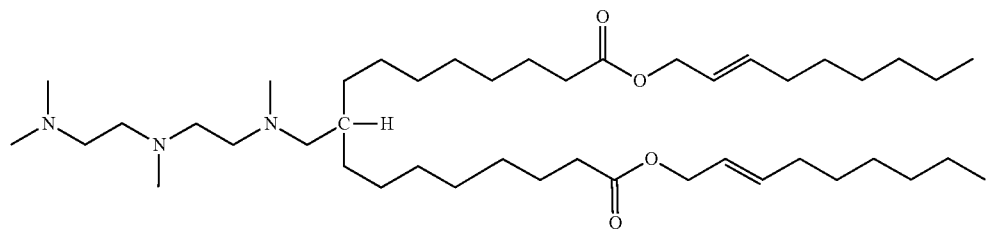
(1-09)
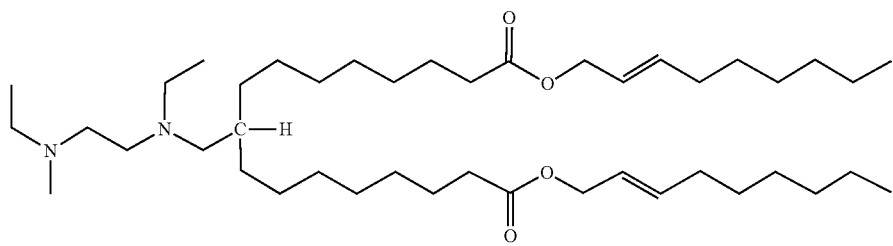
(1-10)
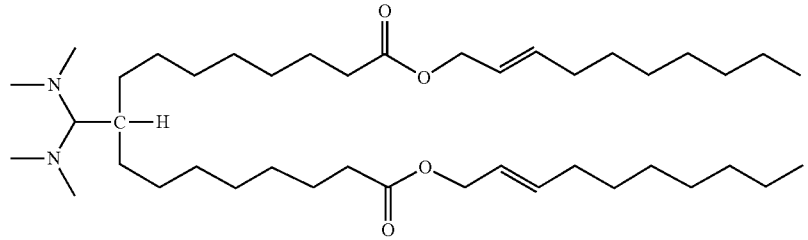
(1-11)
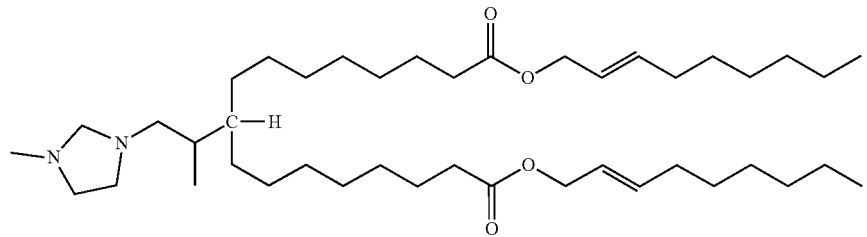
(1-12)
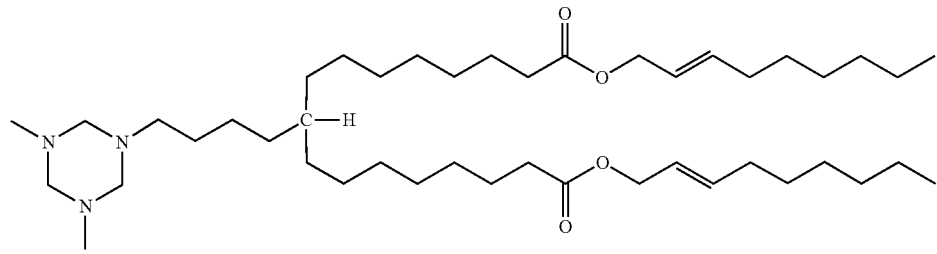

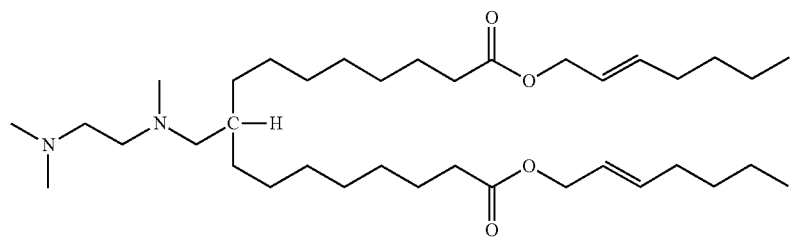
(1-13)
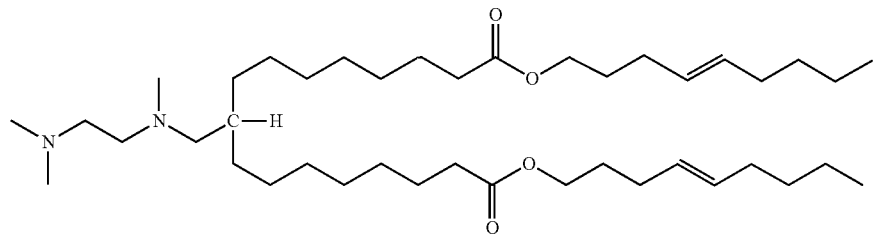
(1-14)
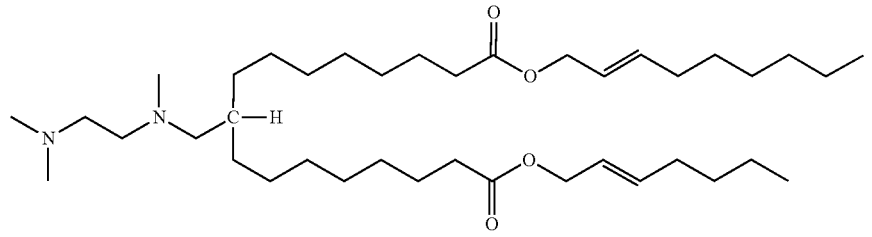
(1-16)
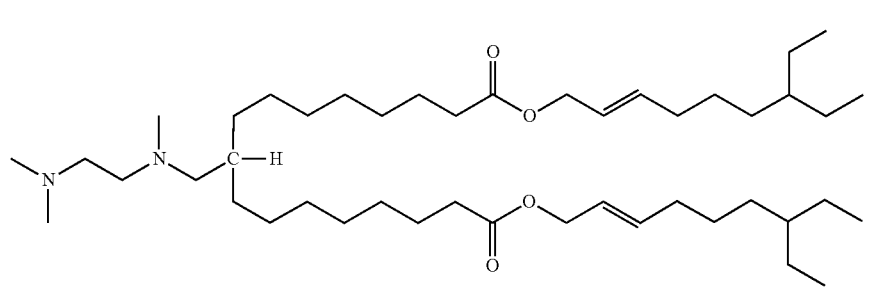
(1-17)
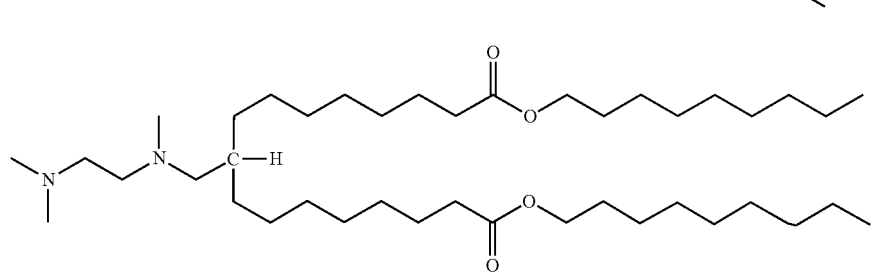
(1-18)
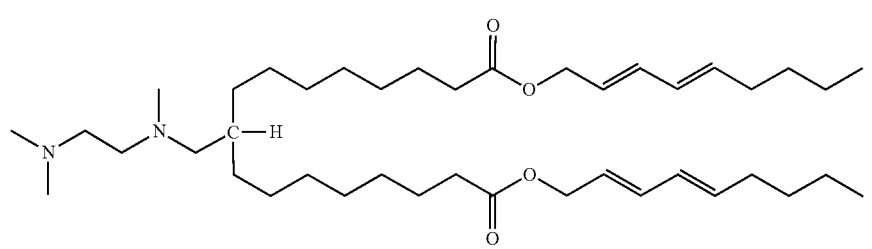
(1-20)

-continued
(1-21)
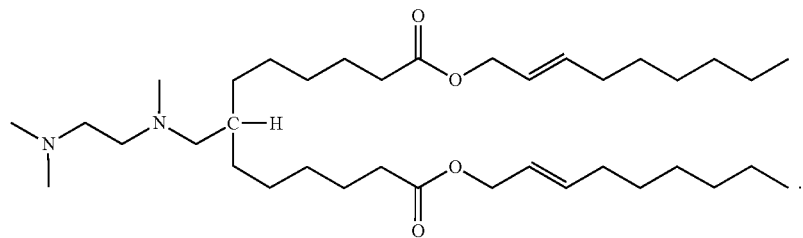
* * * * *